US005553620A

United States Patent [19]

Snider et al.

[11] Patent Number: 5,553,620
[45] Date of Patent: Sep. 10, 1996

[54] INTERACTIVE GOAL-DIRECTED ULTRASOUND MEASUREMENT SYSTEM

[75] Inventors: A. Rebecca Snider, Cockeyesville, Md.; Richard M. Bennett, Half Moon Bay, Calif.; Laurence J. McCabe, Sunnyvale, Calif.; Peter J. Magsig, Mountain View, Calif.; Kane L. Ng, Hayward, Calif.; Lynn M. Purdy, Issaquah, Wash.; Joseph W. Ruffles, San Jose, Calif.

[73] Assignee: Acuson Corporation, Mountain View, Calif.

[21] Appl. No.: 432,870

[22] Filed: May 2, 1995

[51] Int. Cl.⁶ ............................................. A61B 8/00
[52] U.S. Cl. ............................................ 128/660.04
[58] Field of Search ................ 128/660.04, 660.05, 128/710; 395/156, 157, 158, 161, 160, 650; 364/413.22, 413.25; 345/133

[56] References Cited

U.S. PATENT DOCUMENTS 4,612,937 9/1986 Miller ............................ 128/660.05
5,482,050 1/1996 Smokoff et al. .................. 128/660.04

OTHER PUBLICATIONS

"Acuson 128XP Computed Sonography System User Manual for Cardiovascular Applications," Section 9 and 10, 1991, Acuson Corporation.

*Primary Examiner*—George Manuel
*Attorney, Agent, or Firm*—Majestic, Parsons, Siebert & Hsue

[57] ABSTRACT

The use of menu branches associated with a patient's potential condition aids in the accuracy and efficiency of an ultrasound measurement system. The menu branches use a set of suggested measurements to produce results that allow for the evaluation of the potential condition of the patient. The set of suggested measurements can be less than all of the possible measurements for the calculation package. The user no longer has to skip through a large menu full of irrelevant measurement selections. For this reason, the user is less likely to skip pertinent measurements or do time consuming measurements which are irrelevant to evaluate the potential condition. The time savings is important since the user of the ultrasound measurement system may be under severe time pressure.

28 Claims, 17 Drawing Sheets

Cardiac Calculations
Valve Stenosis
Aortic Valve

62

64

M-mode
  IVS insp, exp
  LV d, s
  LVPW d, s
2D-mode
 LV mass, Area Length
  LV epi. Area, d
  LV endo. Area, d
  LV Major Axis, d
 LV mass, Truncated Ellipsoid
  LV epi. Area, d
  LV endo. Area, d
  LV area, A4C, d
  LV Major Axis, d
  LV Semi-major Axis
  LV TSM Axis
  LV Minor Axis
Aortic Doppler
  AoV Vmax
  AoV Peak Grad.
  AoV VTI
  AoV Mean Grad.
  AoV AT
  AoV ET
AoV Continuity Equation
  AoV Vmax
  AoV VTI
  AoV Mean Grad.
  AoV Mean Accel.
  AoV AT
  AoV ET
  LVOT Vmax
  LVOT VTI
  LVOT Vmean
  LVOT Mean Grad.
  LVOT Diameter
PISA AoV
  AoV PISA Radius
  AoV PISA Radius Vel.
  AoV Vmax
  AoV VTI
  AoV Vmean
  AoV Mean Grad.
  AoV Mean Accel.
  AoV AT
  AoV ET
  AoV PISA
  AoV Peak flow

Cardiac Calculations
Valve Stenosis
Pulmonary Valve

PV Doppler
  PV Vmax
  PV Peak Gradient
  PV VTI
  PV Vmean
  PV Mean Grad.
  PV AT
  PV ET
PV Continuity Equation
  PV Vmax
  PV VTI
  PV Mean Grad.
  PV Mean Accel.
  PV AT
  PV ET
  RVOT Vmax
  RVOT VTI
  RVOT Vmean
  RVOT Peak Gradient
  RVOT Diam.
PISA PV
  PV PISA radius
  PV PISA radius vel.
  PV Vmax
  PV VTI
  PV Vmean
  PV Mean Grad.
  PV Mean Accel.
  PV AT
  PV ET
  PV PISA

68

Cardiac Calculations
Valve Stenosis
Tricuspid Valve

TV 2D measurements
  TV Area (planim)
  TV Diameter (A-P)
  TV Diameter (M-L)
TV Continuity Equation
  Proximal VTI
  Proximal Diam.
  TV Vmax
  TV VTI
  TV Mean Grad.
TV Doppler
  TV Vmax
  TV VTI
  TV Mean Grad.
  TV P1/2 T
  TV Decel. Time
PISA TV
  CDI Radius
  Aliasing Velocity
  CDI Funnel Angle
  TV Vmax
  TV VTI
  TV Mean Grad.
  TV PISA Fig. __5-2.__

80a

Cardiac Calculations
Valve Regurgitation
Aortic Valve

M-mode
  LV d, s
2D-mode
  LV Dimensions
    PLAX
      LV Minor Axis d, s
    PSAX, PAP
      LV Area, pap d, s
      LV Minor Axis, pap d, s
    A4C
      LV Major Axis d, s
      LV Minor Axis, pap d, s
      LV Minor Axis, chord d, s
      LV Area d, s
    A2C
      LV Major Axis d, s
      LV Minor Axis, pap d, s
      LV Minor Axis, chord d, s
      LV Area d, s
  LV mass, Area Length
    LV epi. Area, d
    LV endo. Area, d
    LV Major Axis, d
  LV mass, Truncated Ellipsoid
    LV epi. Area, d
    LV endo. Area, d
    LV area, A4C, d
    LV Major Axis, d
    LV Semi-major Axis
    LV TSM Axis
    LV Minor Axis

80b

Cardiac Calculations
Valve Regurgitation
Aortic Valve

AR CD Jet Ratios
  AR Jet Height
  LVOT Height
  AR Jet Area
AR Slope
  AR Slope
  AR DT
  AR V1/2 T
  AR P1/2 T
AR PISA
  PISA Radius
  AR Aliasing Velocity
  AR VTI

Cardiac Calculations
Valve Regurgitation
Aortic Valve

AR Volume by Dop/Dop
  AoV VTI
  AoV Vmean
  LVOT Diameter, s
  RVOT Diameter, s
  PV VTI
  PV Vmean
AR Volume by 2D/Dop
 A4C
  LV Area d, s
  LV Major Axis d, s
  LV Minor Axis, base d, s
 A2C
  LV Area d, s
  LV Major Axis d, s
  LV Minor Axis d, s
  PV Doppler
  PV Vmax
  PV VTI
  PV Mean Grad.
  PV Mean Accel.
  PV Diameter
AR by 2D/2D
 A4C
  LV Area d, s
  LV Major Axis d, s
  LV Minor Axis, base d, s
 A2C
  LV Area d, s
  LV Major Axis d, s
  LV Minor Axis d, s
 RV
  RV Area d, s
  RV Major Axis d, s

81a

Cardiac Calculations
Valve Regurgitation
Mitral Valve

M-mode
  LV d, s
  LA, s
2D-mode
 LA Volumes
  View 1
   LA Area d, s
  View 2
   LA Area d, s
 LV Volumes
  A4C
   LV Area d, s
   LV Major Axis d, s
   LV Minor Axis d, s
  A2C
   LV Area d, s
   LV Major Axis d, s
   LV Minor Axis d, s
  PSAX
   LV Area, pap d, s
   LV Minor Axis, pap d, s
MR PISA
  PISA Radius
  Aliasing Velocity
  MR Vmax
  MR VTI Fig. __7A-2.__

81b

| Cardiac Calculations |
| Valve Regurgitation |
| Mitral Valve |

MR by 2D/Dop
  A4C
    LV Area d,s
    LV Major Axis d, s
    LV Minor Axis d, s
  A2C
    LV Area d, s
    LV Major Axis d, s
    LV Minor Axis d, s
    LVOT VTI
    LVOT Diameter
MR by 2D/2D
  A4C
    LV Major Axis d, s
    LV Minor Axis, base d, s
    LV Area d, s
  A2C
    LV Minor Axis d, s
    LV Minor Axis d, s
    LV Area d, s
    RV Area d, s
    RV Major Axis d, s

82

| Cardiac Calculations |
| Valve Regurgitation |
| Tricuspid Valve |

M-mode
  RVAW, d
2D-mode
  RV Volume
    RV Area d, s
    RV Major Axis d, s
    RVIT Area d, s
    RVOT Area d, s
  RA Volume
    View 1
      RA Area d, s
    View 2
      RA Area d, s
    TR by PISA
      CDI Radius
      Aliasing Velocity
TR by 2D/Dop
  RV Area, method d, s
  RV Major, method d, s
  RVOT VTI
  RVOT Diameter
TR by 2D/2D
  A4C
    LV Area d, s
    LV Major Axis d, s
    LV Minor Axis, base d, s
  A2C
    LV Area d, s
    LV Major Axis d, s
    LV Minor Axis d, s
    RV Area d, s
    RV Major Axis d, s

Cardiac Calculations
Valve Regurgitation
Pulmonic Valve

M-mode
  RV d, s
2D - mode
  RV Volume
    RV Area d, s
    RV Major Axis d, s
    RVIT Area d, s
    RVOT Area d, s
PR by PISA
  CDI Radius
  Aliasing Velocity
  PR VTI

84b

Cardiac Calculations
Valve Regurgitation
Pulmonic Valve

PR by Dop/Dop
  AoV VTI
  PV VTI
  LVOT Diameter
  RVOT Diameter
PR by 2D/Dop
  RV Area d, s
  RV Major Axis d, s
  AoV Vmax
  AoV VTI
  AoV Mean Grad.
  AoV Mean Accel.
  LVOT Diameter
PR by 2D/2D
  LV
    A4C
      LV Area d, s
      LV Major Axis d, s
      LV Minor Axis, base d, s
    A2C
      LV Area d, s
      LV Minor Axis d, s
      LV Minor Axis d, s
  RV
    RV Area d, s
    RV Major Axis d, s
    RVIT Area d, s
    RVOT Area d,s

86

Cardiac Calculations
Valve Regurgitation
Generic PISA

[SITE] PISA
[SITE] CDI Radius
[SITE] Aliasing Velocity
[SITE] VTI

Fig. 7B-2.

88 — Cardiac Calculations
Basic Measurements

M-mode
  RV-LV
  MV
  LV/Ao
  TV
  STIs
2D Dimensions
  PLAX
  PSAX
  Apical
  SSN, Long Axis
2D Volumes
  LV/RV
  LA/RA
LV Mass
  Area/Length
  Truncated Ellipse
Basic Doppler
  Aortic Valve
  Pulmonic Valve
  Mitral Valve
  Tricuspid Valve
  Venous Flow

90 — Cardiac Calculations
Basic Measurements
 M-Mode

RV-LV M-mode
  RVAW d, s
  RV d, s
  IVS d, s
  LV d, s
  LVPW d, s
  PE
MV M-mode
  MVDE
  MV E-F Slope
  MV EPSS
LA/Ao M-mode
  Ao diameter, d
  LA, s
  AoV cusp sep
TV
  TV D-E
  TV E-F
STIs
  LVPEP
  LVET
  RVPEP
  RVET

92 — Cardiac Calculations
Basic Measurements
 2D chamber dimensions

PLAX
PSAX
  PSAX, Chordal level
  PSAX, Papillary level
  PSAX, Aortic Valve Level
Apical
  A4C
  A2C
SSN
  Long Axis
  Short Axis

Cardiac Calculations
Basic Measurements
  2D chamber dimensions
  PLAX

- RVAW d, s
- RV d, s
- IVS d, s
- LV Minor, base d, s
- LV Minor mid d, s
- LVPW d, s
- Ao diameter, d d, s
- LA Diameter d, s
- MV Annulus d, s
- AoV cusp separation
- LVOT Diameter, s
- Aortic sinus, s
- Aorta (st junct), s
- Asc Aorta, s
- LA Area, s
- RA Area, s
- TV Annulus, s
- SVC, insp d, s

96

Cardiac calculations
Basic Measurements
  2D chamber dimensions
  PSAX

- PSAX, Chordal level
  - RVAW d, s
  - RV d, s
  - IVS d, s
  - LVPW d, s
  - LV Area d, s
- PSAX, Papillary level
  - RVAW d, s
  - RV d, s
  - IVS d, s
  - LV d, s
  - LVPW d, s
  - LV Area d, s
- PSAX, AoV Level
  - Aorta, d d, s
  - L Main Coronary
  - L Circ Coronary
  - LAD Coronary
  - R Main Coronary
  - LA Diameter d, s
  - LA Area d, s
  - RA Area d, s
  - Main Pulm Artery d, s
  - RPA Diam., d d, s
  - LPA Diam. d, s
  - AoV Area, planimetry
  - RVOT Diam., s
  - L upper PV
  - L lower PV
  - R upper PV
  - R Lower PV

Cardiac Calculations
Basic Measurements
  2D chamber dimensions
  Apical A4C
  LV Major Axis d, s
  LV Minor Axis, pap d, s
  LV Minor Axis, chord d, s
  LV Area d, s
  RV Major Axis d, s
  RV Minor Axis d, s
  RV Area d, s
  LA Major Axis d, s
  LA Minor Axis d, s
  MV Annulus, d
  LA Area d, s
  RA Area d, s
  TV Annulus, d
  L upper PV
  L lower PV
  R upper PV
  R Lower PV
  RA Major Axis d, s
  RA Minor Axis d, s
A2C
  LV Major Axis d, s
  LV Minor Axis, pap d, s
  LV Minor Axis, chord d, s
  LA Area d, s
  MV Annulus Diam., d
  LA Major Axis d, s
  LA Minor Axis d, s

100

Cardiac Calculations
Basic Measurements
  2D chamber dimensions
  SSN

SSN, Long Axis
  Trans Ao Diam d, s
  Ao Isthmus diam. d, s
  Desc Ao Diam. d, s
  RPA Diam. d, s
  RPA Area d, s
SSN, Short Axis
  Trans Ao Diam d, s
  Trans Ao Area d, s
  SVC Diam. insp, exp
  RPA Diam., d
  LPA Diam, d
  Rt upper PV d, s
  R Lower PV d, s
  L upper PV d, s
  L lower PV d, s

Fig. 8B-1.

| 102 | 104 | 106 |
|---|---|---|
| Cardiac Calculations<br>Basic Measurements<br>  2D Volumes | Cardiac Calculations<br>Basic Measurements<br>  2D Mass | Cardiac Calculations<br>Basic Measurements<br>  Basic Doppler |
| LV Volumes<br>A4C<br>  LV Area d, s<br>  LV Major Axis d, s<br>  LV Minor Axis d, s<br>A2C<br>  LV Area d, s<br>  LV Major Axis d, s<br>  LV Minor Axis d, s<br>PSAX<br>  LV Area, pap d, s<br>  LV Minor Axis, pap d, s<br>RV Volume<br>  RV Area d, s<br>  RV Major Axis d, s<br>  RVIT Area d, s<br>  RVOT Area d, s<br>LA Volumes<br>  View 1<br>    LA Area d, s<br>  View 2<br>    LA Area d, s<br>RA Volumes<br>  View 1<br>    RA Area d, s<br>  View 2<br>    RA Area d, s | LV mass, Area Length<br>  LV epi. Area, d<br>  LV endo. Area, d<br>  LV Major Axis, d<br>LV mass, Truncated Ellipsoid<br>  LV epi. Area, d<br>  LV endo. Area, d<br>  LV area, A4C, d<br>  LV Major Axis, d<br>  LV Semi-major Axis<br>  LV TSM Axis<br>  LV Minor Axis | Aortic Valve<br>  AoV Vmax<br>  AoV Vmean<br>  AoV Peak Grad.<br>  AoV VTI<br>Pulmonic Valve<br>  PV Vmax<br>  PV Vmean<br>  PV Peak Gradient<br>  PV VTI<br>Mitral Valve<br>  MV Vmax<br>  MV Mean Grad.<br>  MV VTI<br>Tricuspid Valve<br>  TV Vmax<br>  TV VTI<br>  TV Mean Grad.<br>Venous Flow<br>  SVC Vmax<br>  IVC Vmax<br>  RUPV Vmax<br>  RLPV Vmax<br>  LUPV Vmax<br>  LLPV Vmax |

Fig. 8B-2.

INTERACTIVE GOAL-DIRECTED ULTRASOUND MEASUREMENT SYSTEM

BACKGROUND OF THE INVENTION

The present invention relates to ultrasound measurement systems and methods of making measurements from ultrasound images. Ultrasound measurement systems typically are used to make measurements from a displayed ultrasound image. The ultrasound image is provided from an ultrasound imaging system, a recording device, or an off-line storage system.

Ultrasound imaging systems can produce images of a patient's internal organs for display on a monitor. The information measurable from the monitor depends on the operational mode of the displayed image. For example, a two-dimensional mode (2-D), sometimes known as B-mode, allows for the measuring of distances, areas and volumes off of the display screen; a Doppler mode allows for the obtaining of measurements that indicate velocities from the display screen; a motion mode (M-Mode) shows the movement of structures in one-dimension over time.

One prior system for making ultrasound measurements is to use a ruler or hand-held calipers to make the desired measurements from a display screen. By knowing the scale of the screen view, the physical distance on the screen can be manually converted into a desired measurement. A relatively large margin of error is associated with the use of the hand-held calipers or rulers. Additionally, the manual computation of the results, either with a calculator or with pen and paper, introduces another potential error.

Other ultrasound measurement systems use computerized tools. These systems use graphical measurement tools that appears on the display screen and allow for the measurement of structures in images displayed on the display screen. Ultrasound measurement systems that use computerized tools include the Acuson 128XP Computed Sonography System, described in the "Acuson 128XP Computed Sonography System User Manual for Cardiovascular Applications", sections 9 and 10, copyright 1991 by ACUSON Corporation, incorporated herein by reference. In the Acuson 128XP Computed Sonography System, when a measurement is selected from a menu on a display screen, the pertinent computerized graphical tools are shown on the display screen. These graphical tools allow a desired measurement to be made off of the display screen. Measurements can be done in different operational modes and the measurement is interpreted accordingly.

SUMMARY OF THE INVENTION

The present invention is a goal-directed computerized ultrasound measurement system. The measurement menus of the ultrasound measurement system of the present invention that allow for the selection of measurements are arranged according to the reasons for which someone would use the ultrasound measurement system. The present invention does this by associating some of the measurement menus with potential conditions of the patient.

Typically, the operator of an ultrasound measurement system will use the system to help evaluate whether a patient has a certain condition. These potential conditions can be relatively broad categories such as valvular regurgitation or can be narrower categories such as mitral valve regurgitation. The potential condition may be identified before the examination begins or the user may identify a potential condition during the examination due to the ultrasound image or preliminary results.

The menu structure of the ultrasound measurement system of the present invention allows the user to select a menu branch associated with a potential condition. This menu branch can be a single measurement menu or can include submenu(s) and measurement menus linked to these submenu(s). The menu branch associated with a potential condition allows for the selection of a set of measurements suggested for that potential condition. A measurement menu in the menu branch can contain some or all of this set of suggested measurements. In a preferred embodiment, the set of suggested measurements contains less than all of the measurements that can be made by the system. The set of suggested measurements can be used to produce results that aid in the determination of whether the patient has the potential condition.

Prior ultrasound measurement systems do not associate a potential condition of the patient with measurement menus. Some prior ultrasound measurement systems request that the user input a diagnosis as background information along with the patient's name and I.D. number. The prior ultrasound measurement systems do not use this diagnosis information in arranging the menus of the ultrasound measurements or provide a set of suggested measurements for a potential condition. Prior systems force the user to review the list of all possible measurements in order that the user can select the desired measurements even if a diagnosis is input.

Prior ultrasound measurement methods are time consuming to perform, and require that the user have a comprehensive knowledge of what to measure for each potential condition. Many measurements not germane to the context of a given patient are customarily skipped by a knowledgeable user of the prior ultrasound measurement systems in the interest of efficiency. The menu structure of the ultrasound measurement system of the present invention is preferably arranged such that measurements non-essential to evaluating a potential condition are not shown to the user. Only the set of suggested measurements for a given condition are shown and selectable when the user has selected a potential condition. In this way, the user does not have to recall a comprehensive list of measurements appropriate to the condition.

Additionally, since in the prior methods many measurements were skipped by the ultrasound measurement users, a measurement which is required to produce a calculated value may be easily overlooked or forgotten during the measurement process. This could require the retesting of the patient; remeasurement from an archive medium which is less accurate than measurements made while connected to an ultrasound image measuring system; or even worse for accuracy, the gross estimation of a skipped measurement and the manual recalculation of the value. The ultrasound measurement system of the present invention will prompt the user to make the measurements required for the calculations relevant to the potential condition. The user need not know all the measurements required for complex calculations (e.g. LV Mass) to generate the end result. Prior systems used view or mode related menus which required knowledge of the measurements required for such complex calculations.

The ultrasound measurement system of the present invention can also arrange the results including calculations and relevant measurements in a manner appropriate for the potential condition for which the measurements were taken. This arrangement makes it easier for the user to evaluate the potential condition. In the prior systems, a good deal of non-germane data or textural placeholders and empty numerical data must be visually scanned and inspected to obtain the desired information.

The advantages of the Ultrasound Measurement System of the present invention can be illustrated with a few typical scenarios. Consider a post-surgical Coronary Artery Bypass patient with signs of left ventricular dysfunction for which an echocardiagram is ordered to access the function. The patient is in a crowded room with barely enough room for the patient and nursing staff when the ultrasound system is wheeled in with the sonographer. The patient is attached to a ventilator and five intervenous lines; a urinary catheter and other drainage tubes are in place. The patient has a chest incision with staples and bandages, and is restricted to a supine position (not the best position for obtaining images). A duplicate set of electrocardiogram (ECG) patches must be placed, because the nurses do not want the patient off the ECG monitor. There is very limited access to the patient for imaging.

Tension is high. The nursing staff wants access to the patient. They want the ultrasound people and system out of the room as soon as possible. The patient is having severe arrhythmias, and the nurses do not want the ECG monitors disconnected.

The ultrasound measurement system user needs to get in and out of the room as quickly as possible with all the pertinent clinical information to make a diagnosis and form a clinical strategy. During the evaluation, the ultrasound measurement system of the present invention provides the sonographer with a check-list of suggested measurements to assess the left ventricular function. Since the suggested measurements are provided to the user, the exam time can be reduced and a complete set of results ensured.

The menu provided for assessment of LV systolic function is shown below. Measurements associated with wall scoring analysis (not shown) may also be used.

LV Systolic Function
M-mode
LV Diameter in diastole and systole
MV EPSS
LVET
LVPWD
LV Major Axis, s
2D
PSAX
LV Minor Axis, chord in diastole and systole
LV Minor Axis, pap in diastole and systole
LV Area, pap in diastole and systole
A4C
LV Area in diastole and systole
LV Major Axis in diastole and systole
LV Minor Axis in diastole and systole
A2C
LV Area in diastole and systole
LV Major Axis in diastole and systole
LV Minor Axis in diastole and systole
Doppler
MR Slope
AoV Mean Accel.
AoV AT
AoV ET Using the menu above, the specific measurements that are needed to assess the left ventricular function are obtained. Productivity and accuracy are increased. Repeat examinations are typically avoided, due to the check-list approach of the ultrasound measurement system of the present invention. All related result values are presented together in a clinically sensible arrangement, making the differential diagnostic process more straightforward for the physician interpreting the results. The goal-directed approach of the ultrasound measuring system is especially useful since a sonographer in the cardiac setting usually works independently and then presents the results to a cardiologist after the examination.

A second scenario concerns a newborn infant, shocky with poor perfusion. Murmur and diminished pulses are noted. The infant is to be evaluated for aortic stenosis.

The infant is in a crowded neonatal intensive care room with several isolettes of premature and newborn infants, all critically ill. Several nursing staff and physicians are in the room. There is limited work space in the isolette.

As in the first scenario, tension is high. The newborn infant is critically ill and there is a need to determine a diagnosis and course of clinical strategy.

Aortic stenosis is selected as a potential condition on the ultrasound measurement system. The ultrasound system now steps the operator through a goal oriented examination, systematically assessing the heart for aortic stenosis. The ultrasound measurement system prompts the operator to make the measurements that aid a doctor in the determination of the severity of the aortic stenosis, whether the aortic stenosis is valvular, subvalvular or supravalvular, and whether it is a critical aortic stenosis or not.

In critical aortic stenosis, the output is decreased, therefore, peak gradients from Doppler can be misleading (low values). The ultrasound measurement system of the present invention would prompt the user to make measurements in the Valvular Stenosis, Aortic Valve area. The suggested measurements for Valvular Stenosis, Aortic Valve area are a combination of M-mode, 2-D and Doppler measurements that provide for a rapid, non-invasive assessment in the diagnosis of the anatomic type and severity of aortic stenosis. As discussed in Snider, "Echocardiography in Pediatric Heart Disease", Year Book Medical Publishers, Inc., the gradients alone in this case would not reflect the actual severity of critical aortic stenosis. The measurements prompted by the ultrasound measurement system in a preferred embodiment are:

Valve Stenosis
Aortic Valve
M-Mode
IVS in diasrole and systole
LV in diastole and systole
LVPW in diastole and systole
2D
LV mass, Area Length
LV epi. Area, in diastole
LV endo. Area, in diastole
LV Major Axis, in diastole
LV mass, Truncated Ellipsoid
LV epi. Area, in diastole
LV en do. Area, in diastole
LV area, A4C, in diastole
LV Major Axis, in diastole
LV Semi-major Axis
LV TSM Axis
LV Minor Axis
Aortic Doppler
AoV Vmax
AoV Peak Grad.
AoV VTI
AoV Mean Grad.
AoV AT
AoV ET
AoV Continuity Equation AoV Vmax
AoV VTI
AoV Mean Grad.
AoV Mean Accel.
AoV AT
AoV ET
LVOT Vmax
LVOT VTI
LVOT Vmean
LVOT Mean Grad.
LVOT Diameter
PISA AoV
AoV PISA Radius
AoV PISA Radius Vel.
AoV Vmax
AoV VTI
AoV Vmean
AoV Mean Grad.
AoV Mean Accel
AoV AT
AoV ET
AoV PISA
AoV Peak flow The ultrasound measurement system of the present invention allows for the rapid, accurate assessment of whether the aortic stenosis is critical. If critical aortic stenosis is indicated, the physician needs to plan the appropriate clinical course of action, which usually includes the possibility of emergency surgery.

This second scenario illustrates the advantage of the ultrasound measurement system of the present invention for an infant with critical aortic stenosis. Had the sonographer or physician only measured the gradient, the values would be within the normal ranges. The gradient calculation alone would not give an accurate clinical picture, because the gradient calculation is dependent on the transvalvular flow, which in this case is severely diminished. Evaluating the left ventricular function, as prompted by the suggested measurements for aortic stenosis in the ultrasound system of the present invention, is essential to determine the critical nature of the aortic stenosis.

The ultrasound measurement system provides for a rapid, comprehensive assessment of the aortic valve and left ventricle in a critical aortic stenosis case, which may otherwise be incorrectly graded in severity.

BRIEF DESCRIPTION OF THE DRAWINGS

The above and other features and aspects of a present invention will become more apparent upon reading the following detailed description in conjunction with the accompanying drawings, in which:

FIGS. 7A–D are diagrams showing the measurements associated with valvular regurgitation in the preferred embodiment of the present invention shown in FIG. 4.

FIGS. 8A–B are diagrams showing the "basic" measurements in the preferred embodiment of the present invention shown in FIG. 4.

DEFINITIONS display screen- device used to present information to the user; the display screen can include but is not limited to monitors, printers, liquid crystal displays, and light emitting diode displays.

input device- input devices include but are not limited to keyboards, mouses, trackballs, soft keys, voice activation systems and touch screen systems.

menu branch- a single menu or linked group of menus potential condition- a possible condition, malady or problem of a patient which is to be examined or evaluated. Potential conditions include conditions that the operator desires to rule out. Anatomical regions by themselves should not be considered potential conditions. Thus "heart" or "heart problem" are not potential conditions, while "valvular stenosis" or "mitral valve regurgitation" are potential conditions.

ultrasound measurement- includes measurements made from an ultrasound image; the selection of an ultrasound measurement can include the prompting of the system to prepare to make this ultrasound measurement.

ultrasound measurement system- apparatus for making measurements from an ultrasound data or image. The ultrasound image can be provided from an ultrasound imaging system, a recording device, or an off-line storage system that is not considered part of the ultrasound measurement system.

DETAILED DESCRIPTION OF THE DRAWINGS

Figure 1:
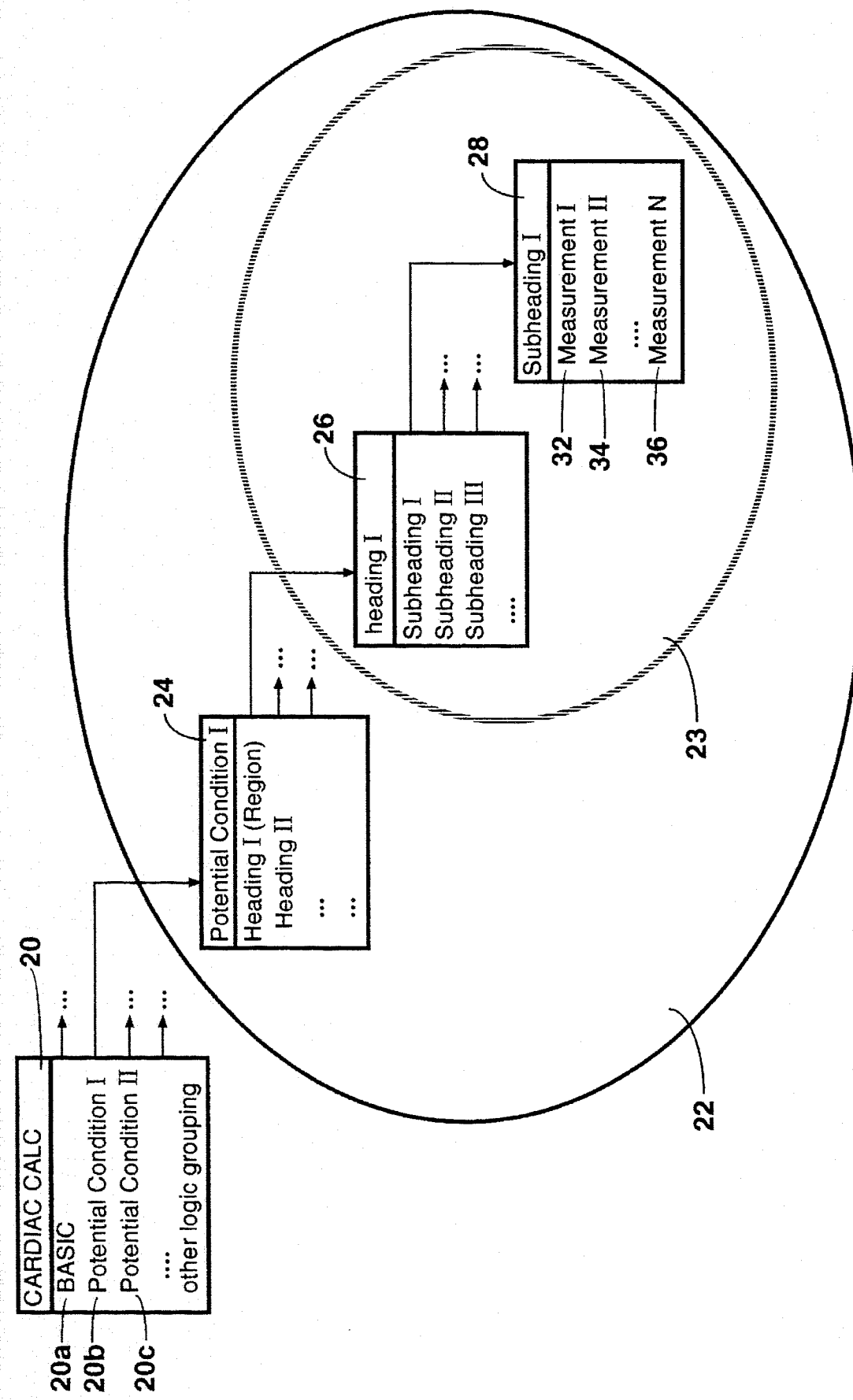
FIG. 1 is a diagram showing an ultrasound measurement menu structure of the present invention.

FIG. 1 is a diagram illustrating the menu structure of the present invention. The ultrasound measurement system of the present invention is in the preferred embodiment focused on cardiac calculations. Other areas for which the ultrasound measurement system may be useful include obstetrics, vascular, and general abdominal imaging applications.

When cardiac calculations is selected, menu 20 lists selectable logical categories. These logical categories in main menu 20 can include a basic category 20a, potential conditions such as Potential Condition I and Potential Condition II, as well as other categories that are not necessarily potential conditions. Associated with each of the groupings in the main menu 20 is a menu branch that contains ultrasound measurements selections that are selectable by the user. Menu branch 22 associated with Potential Condition I is shown in FIG. 1. Menu branches can include a single menu or a group of menus.

The menu structure of the present invention is different from the prior art because menu branches can be associated with a potential condition. Suggested measurements for the potential condition including measurements 32, 34 and 36 can be selected in the branch 22 associated with Potential Condition I. The measurements associated with a potential condition, such as Potential Condition I in the menu branch 22, are preferably not all of the measurements that can be selected using the system. Even the measurements of the menu branch associated with the basic group may contain less than all of the measurements. The basic measurements can be the measurements which would be suggested for a general examination of an anatomical region, such as the heart.

In the menu structure shown in FIG. 1, a category from list 20 is selected. If Potential Condition I is selected, menu 24 will appear. A heading is then selected from menu 24. If heading I is selected, then menu 26 listing subheadings will appear. If subheading I is selected list 28 of the measurements will be shown.

The measurement menu structure shown in FIG. 1 allows the user to logically step through the suggested measurements for a potential condition. The heading and subheading are logical groupings that can include sub-regions, ultrasound operation mode, or a specific calculation. Menu 24 and 26 are sub-menus that provide links to other menus. Menus can include both links to other menus and measurements.

Note that the headings and sub-headings may further define another potential condition. For example if Potential condition I is "valve regurgitation" then heading I may be "mitral valve" so that another potential condition "mitral valve regurgitation" is associated with the menu branch 23. Menu branch 23 is also a part of menu branch 22. The set of suggested measurements in menu branch 23 is sub-set of the measurements selectable from menu branch 22.

Figure 2:
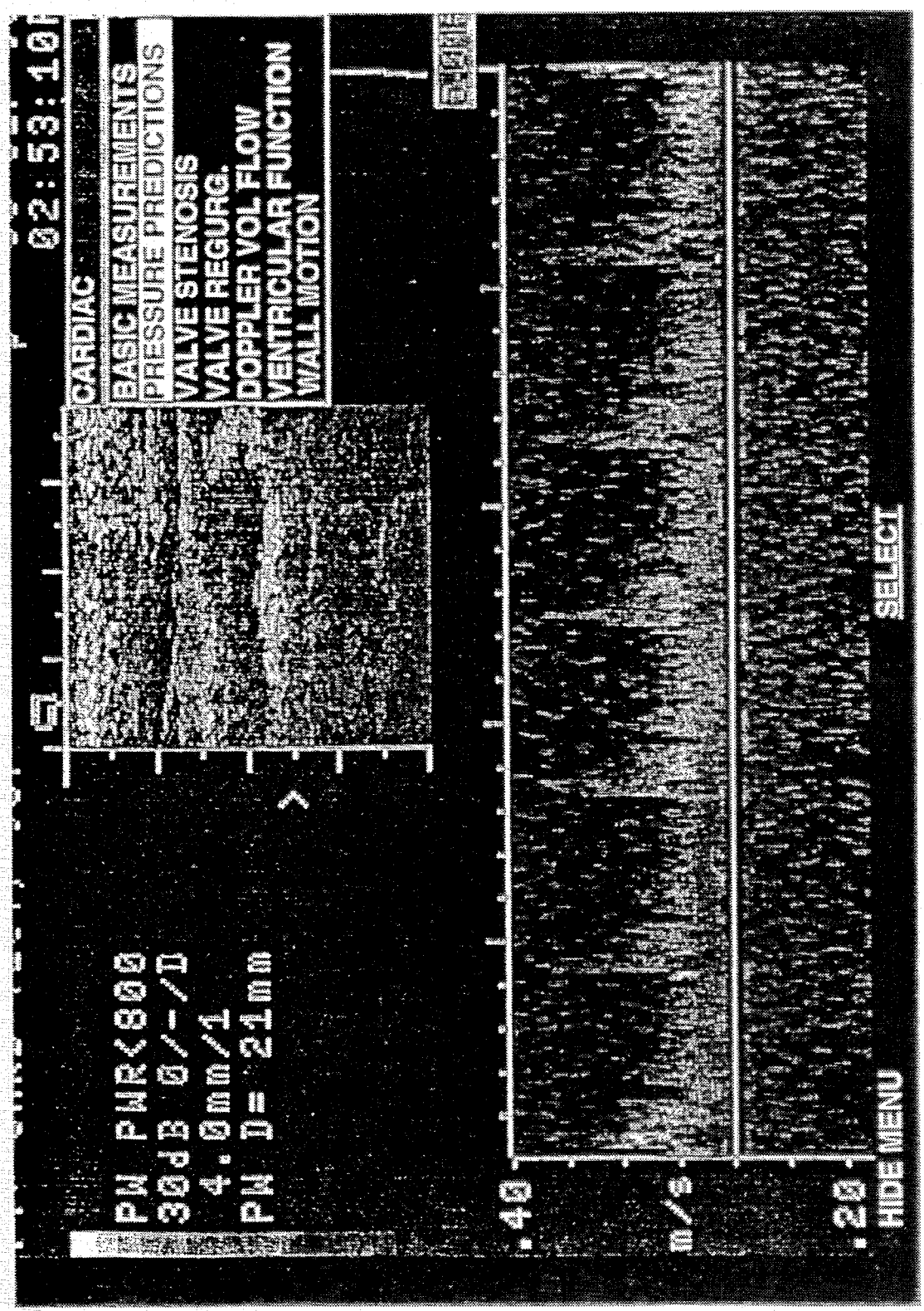
FIG. 2 is a simulated view of a display from a display screen showing the displayed menu choices.

FIG. 2 is a simulated view of a display screen showing displayed main menu choices. Using a keyboard, trackball or mouse, the desired logical category can be selected. In FIG. 2, the selection for pressure predictions is marked and can be selected. The logical category shown in the menu of FIG. 2 include potential conditions such as valve stenosis and valve regurgitation.

Figure 3:
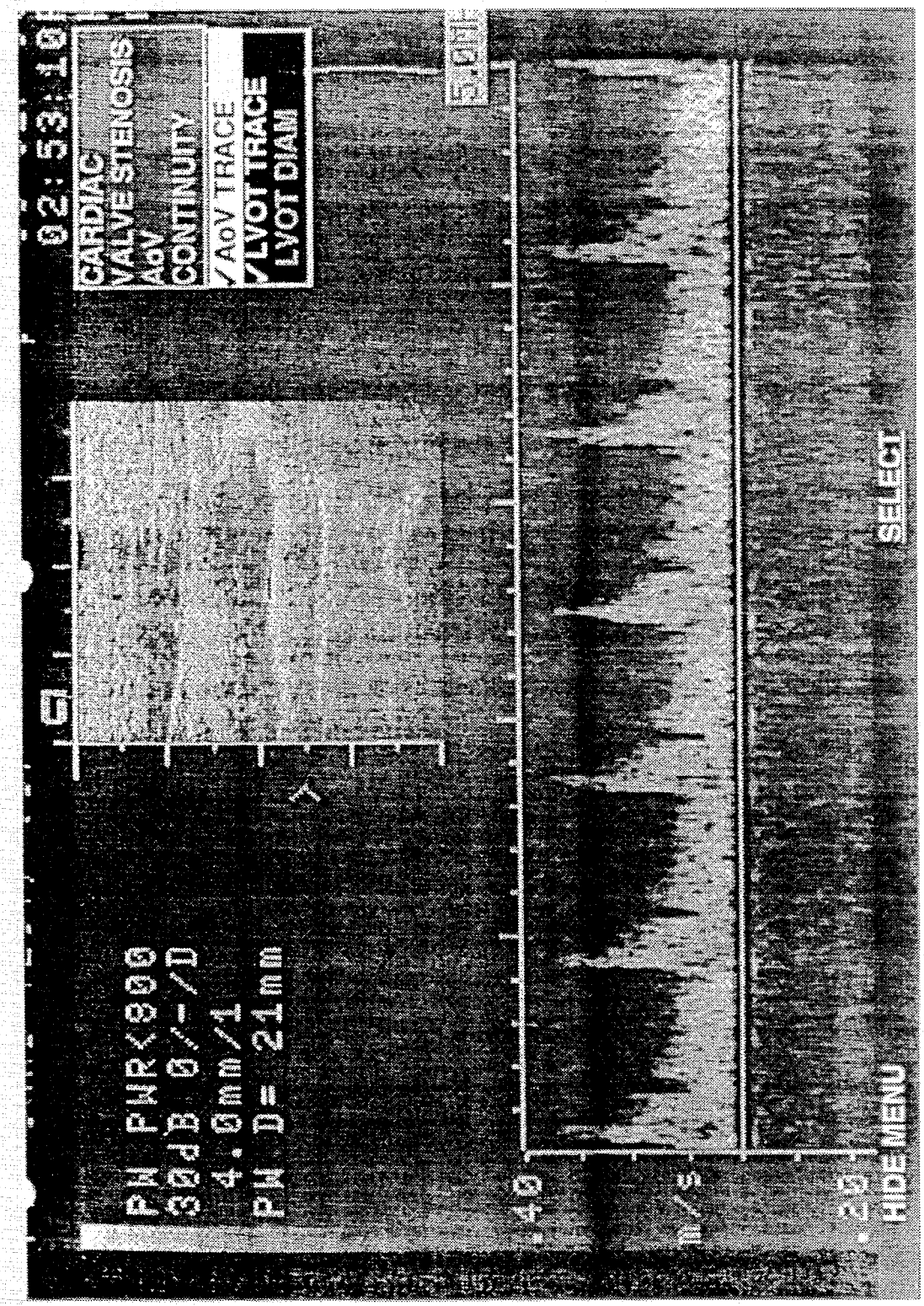
FIG. 3 is a simulated view of a display on a display screen showing the menu after selection of several choices.

FIG. 3 is a simulated view of a display screen showing the menu display after several menu selections. In this case, the category for the potential condition, "valve stenosis" is selected. Additionally, the heading for the region aortic valve (AoV) and the subheading for the continuity equation are selected. At this point, measurements such as AoV TRACE and LVOT TRACE can be selected. LVOT DIAM is shown in gray, since the ultrasound operational mode needs to be switched before selecting this measurement. The user can return to any other menu in the menu structure by selecting the heading or category shown in the menu of FIG. 3. The user can go through all of the measurements associated with a potential condition such as the "valve stenosis" or "aortic valve stenosis" in order to produce the results that are necessary to evaluate the potential condition.

As done in prior ultrasound measurement systems, when a measurement, such as the AoV TRACE, is selected, the appropriate computerized measurement tools will appear on the display screen. The computerized measurement tools can be used to make the desired measurements, these measurements are stored for display and for calculation of results.

Figure 4:
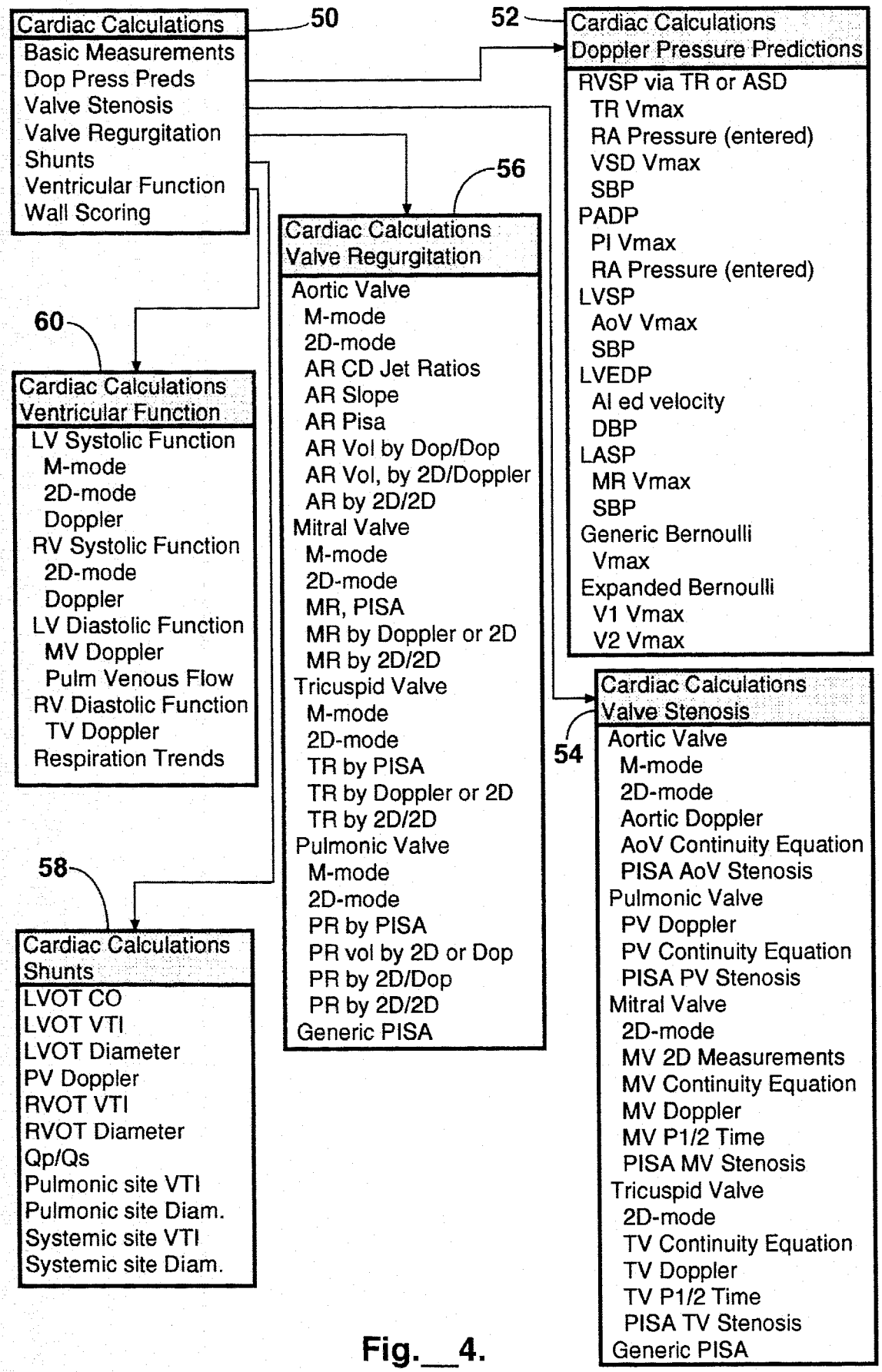
FIG. 4 is a diagram of the menu structure of a preferred embodiment of the present invention.

FIGS. 4–8 show the menu structures and measurements for a preferred embodiment of the present invention which is used to produce cardiac calculations. FIG. 4 is a diagram of a menu structure for a preferred embodiment of the present invention. Menu 50 shows the list of the categories of the cardiac calculations. These categories include the basic measurements, Doppler pressure predictions, valvular stenosis, valvular regurgitation, shunts, ventricular function and wall scoring. Valvular stenosis is the narrowing of a valvular orifice that obstructs outflow. Valvular regurgitation is a retrograde flow of blood through a heart valve. A shunt is a congenital defect that allows for flow between structures or chambers including e.g. interatrial septal, ventricular septal, atrioventricular septal, patent ductus, and coronary sinus fistula. Also shown in FIG. 4 are the listings for the Doppler pressure predictions 52, valvular stenosis 54, valvular regurgitation 56, shunts 58 and ventricular function 60. The abbreviations used in FIGS. 4–8 are expanded in Appendix I.

Figures 1, 5:
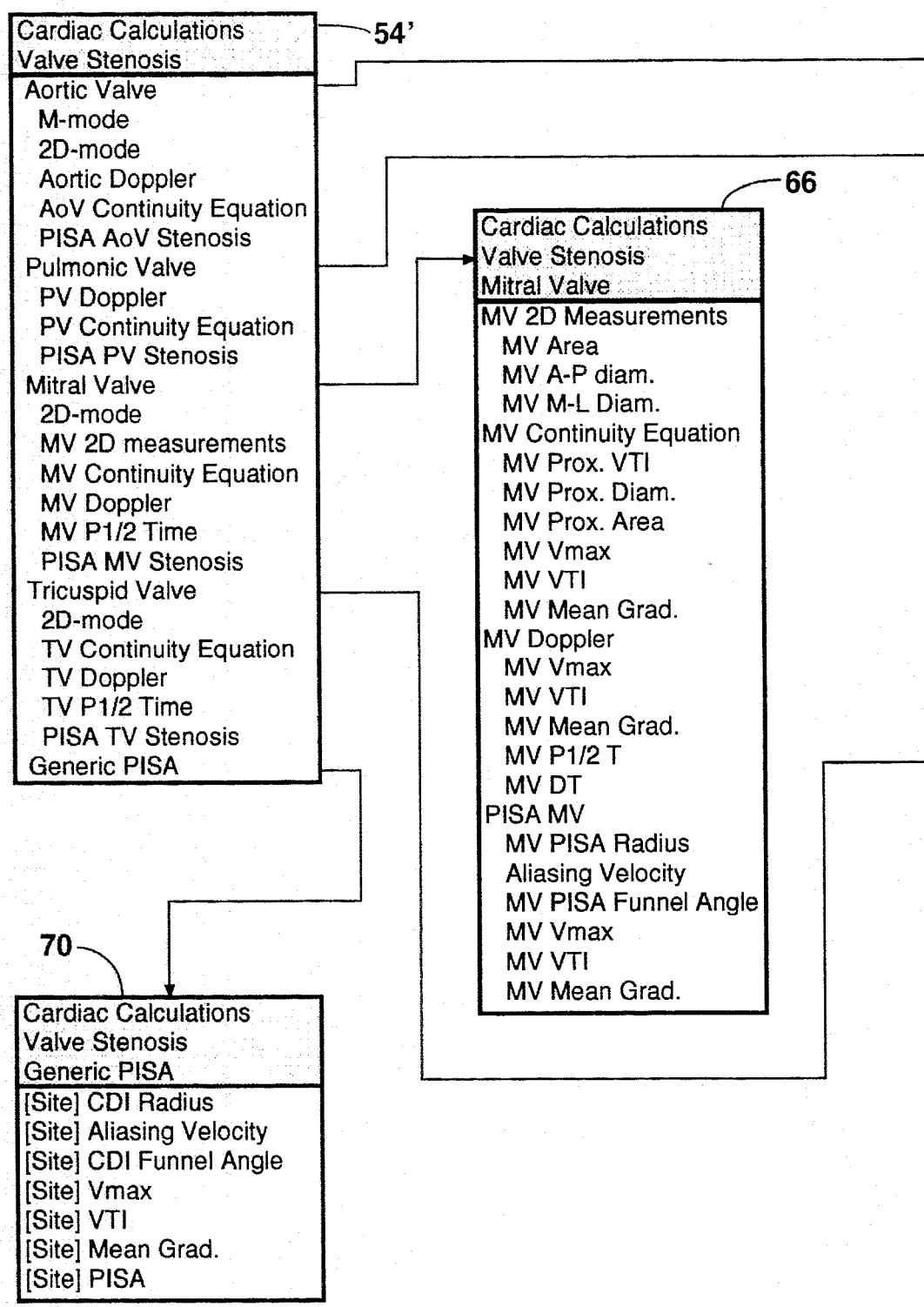
FIG. 5 is a diagram showing the measurements associated with valvular stenosis in the preferred embodiment of the present invention shown in FIG. 4.

FIGS. 5–8 show the measurements associated with the logical groupings. FIG. 5 lists the measurements associated with valvular stenosis. The measurements associated with the valvular stenosis are broken down into aortic valve measurements 62, pulmonary valve measurements 64, mitral valve measurements 66, tricuspid valve measurements 68 and generic proximal isovelocity surface area (PISA) measurements 70.

Figure 6:
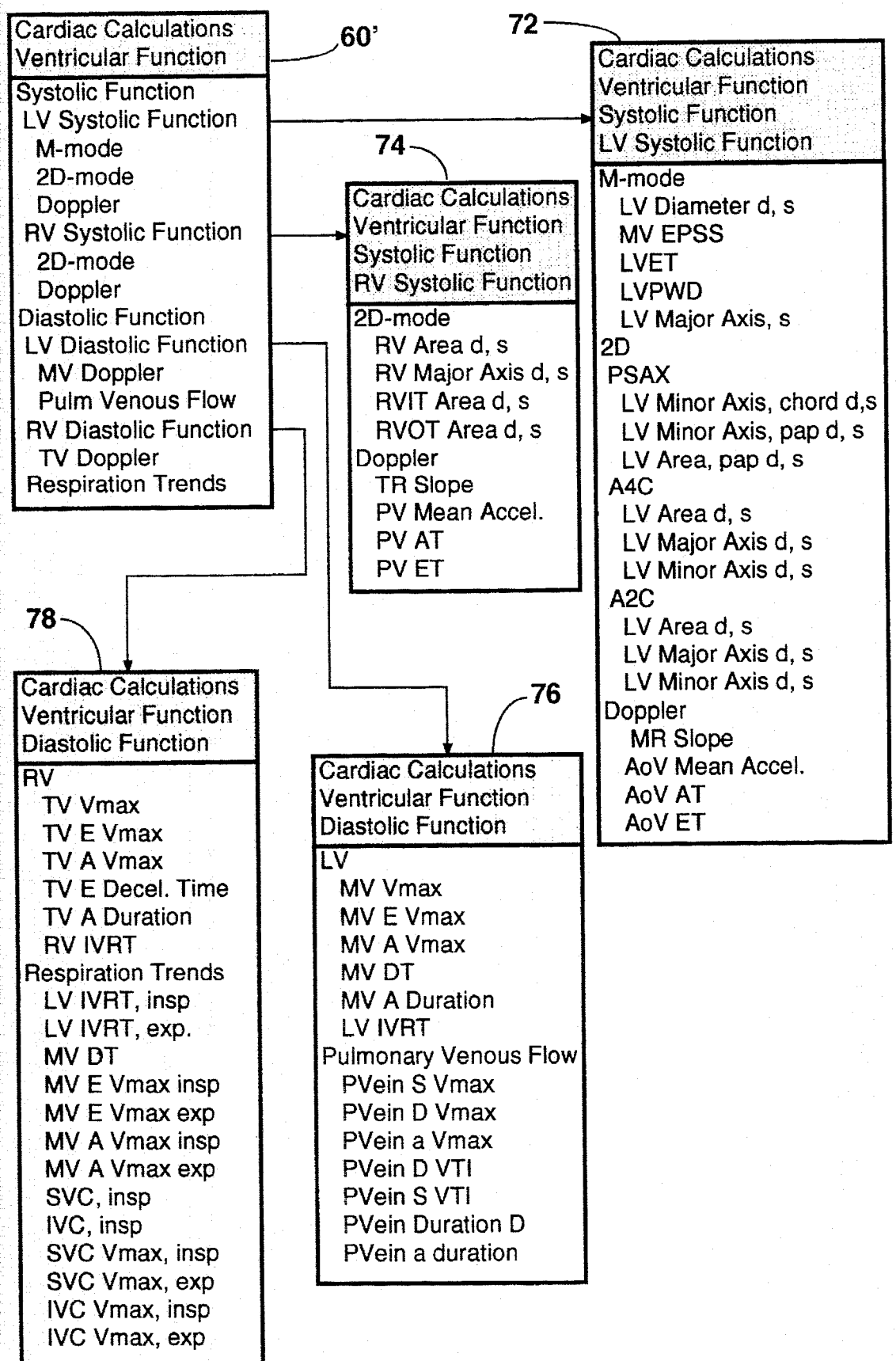
FIG. 6 is a diagram showing the measurements associated with ventricular function in the preferred embodiment of the present invention shown in FIG. 4.

FIG. 6 is a diagram showing the measurements associated with the ventricular function category. The measurement lists include LV systolic function 72, RV systolic function 74, LV diastolic function 76, RV diastolic function 78.

FIGS. 7a and 7b list the measurements associated with valvular regurgitation. The lists include aortic valve measurements 80a, 80b and 80c; mitral valve measurements 81a and 81b; tricuspid valve measurements 82; pulmonary valve measurements 84a and 84b; generic PISA measurements 86.

FIGS. 8a–8b disclose the measurements associated with the "basic" measurement logical grouping. List 88 shows header and sub-header selections. The "Basic" measurements include "M-mode" or motion mode measurements 90, 2D chamber dimensions measurements 92, 2D chamber dimensions parasternal long axis (PLAX) 94, 2D chamber dimensions parasternal short axis (PSAX) 96, 2D chamber dimensions Apical 98, 2D chamber dimensions suprasternal notch (SSN) 100, 2D volumes 102, 2D mass measurements 104, basic Doppler measurements 106.

The user of the ultrasound measuring system of the present invention can customize the lists of measurements by disabling specific tests. The prior 128XP Acuson product also has this ability. Disabled measurements are not displayed to the user for selection.

The calculations involving the measured values can be done automatically in the background as the measurements required in a given calculation are completed. The calculated values are then stored for later display. The calculations used in the system are typically functions of the measurements made in the system. Additional required variables can be input by the user. A list of calculations used in the preferred embodiment of the present invention is shown in Appendix II. Additional calculations can be added as suggested by users. These calculations are obtained from publicly available articles and textbooks. Examples of many of these equations are given in section 10 of the "Acuson 128XP Computed Sonography System User Manual for Cardiovascular Applications". The suggested measurements for a potential condition are chosen such that the desired results for evaluating the potential condition can be displayed after the suggested measurements are made. The results can be arranged for display according to the potential condition being evaluated. This allows for the logical display of results to the user. Non-pertinent results can either be not displayed or displayed less prominently.

Figure 9:
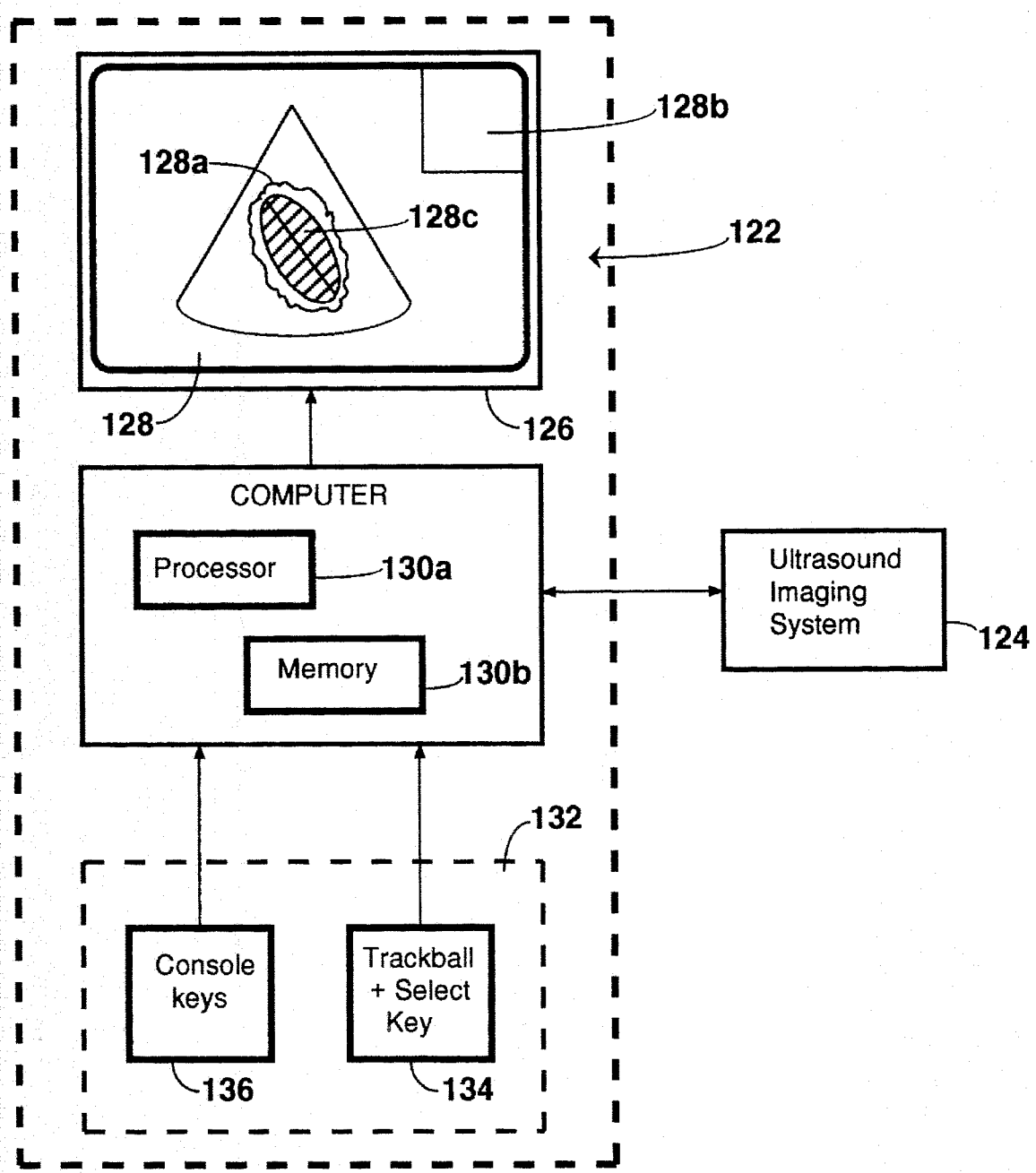
FIG. 9 is a diagram of an apparatus of the present invention showing an ultrasound measurement system along with an ultrasound device.

FIG. 9 is a diagram of an ultrasound measurement system 122 connected to the ultrasound imaging system 124. The ultrasound imaging system 124 is responsible for the acquisition and presentation of the actual ultrasound image from which the measurements are taken. The image is placed on display 128 of display screen 126. This image may be, for example, a two-dimensional image 128*a* of a valve. The display screen 128 is preferably a high quality monitor, such as that available from the Barco company. The ultrasound imaging system 124 can be controlled by the same computer 130 used for the ultrasound measurement system or alternately a second computer (not shown) can be used to interface with the ultrasound measurement system processor or computer. In a preferred embodiment, the ultrasound imaging system control software and the measurement systems calculation software are placed on the same computer 130 so that the programs can easily interface with one another. Preferably the system control software processes include an operating system, such as the UNIX operating system, and a graphics system, such as the X-windows graphics server. The graphic system is loaded into the processor 130*a* of the computer 130 and controls the display 128 on the display screen 126. Processor 130*a* should be powerful enough when it is configured with the operating system, graphics system, and other hardware, to provide a sufficiently responsive user interface. "Responsiveness" is somewhat subjective but most developers are familiar with sources of guidelines, such as the Human Factors Society and the Association for Computing Machinery Special Interest Group on Computer Human Interaction (ACM SIGCHI). Processor 130*a* is in a preferred embodiment a 486 microprocessor.

The measurement systems calculation software (CalcApplication) is stored in memory 130*b* of the computer 130. In a preferred embodiment the memory 130*b* includes a hard disk on which the configuration information which determines the specific contents and organization of a particular calculation package is stored. The hard disk can also be used as a general resource by other subsystems. The CalcApplication software module acts as an interface between the calculation system and an ultrasound imaging device. The CalcApplication software module includes subcomponents which are detailed in FIG. 10. The CalcApplication software module coordinates the actions of the software subcomponents and the other components of the calculation system to affect the behavior of the calculation system.

In a preferred embodiment, the input devices 132 for the ultrasound measurement system include the track-ball and select key 134 and the console keys 136. Other possible input devices include voice recognition systems, touch screen systems and any other way to control the menu 128*a* displayed on the display screen 126. The track ball 134 provides a means for manipulating the graphical tools. Typically, the user make selections from the menu region 128*b* displayed on the display 128 until a measurement is selected. When a measurement is selected the appropriate graphical representation tool such as the ellipse 128*c* appears on the display screen 126. The track ball 134 can be used for matching the elliptical graphical tool 128*c* with the area of valve 128*a* displayed on the display screen 126. Using the select keys and the track ball, the center and different axes of the elliptical measuring device can be maneuvered. Once the elliptical device 128*c* matches the area of the valve 128*a*, the user can press a button to capture this measurement and the area defined by the elliptical tool 128*c* is automatically stored and is available for making calculations. Alternately, the user can use the trace function to trace the actual area of the chamber or valve. Examples and descriptions of graphical tools that can be used with the present invention are discussed in section 9 of the "Acuson 128XP Computed Sonography System User Manual for Cardiovascular Applications".

In addition to an ultrasound imaging system 124, an off-line recording or VCR recording of the ultrasound data could be used. In this way, the measurements can be made after the patient has already been examined. The disadvantage of this method is that the measurements may be somewhat less accurate, due to degradation of the image quality on the second generation image source.

Figure 10:
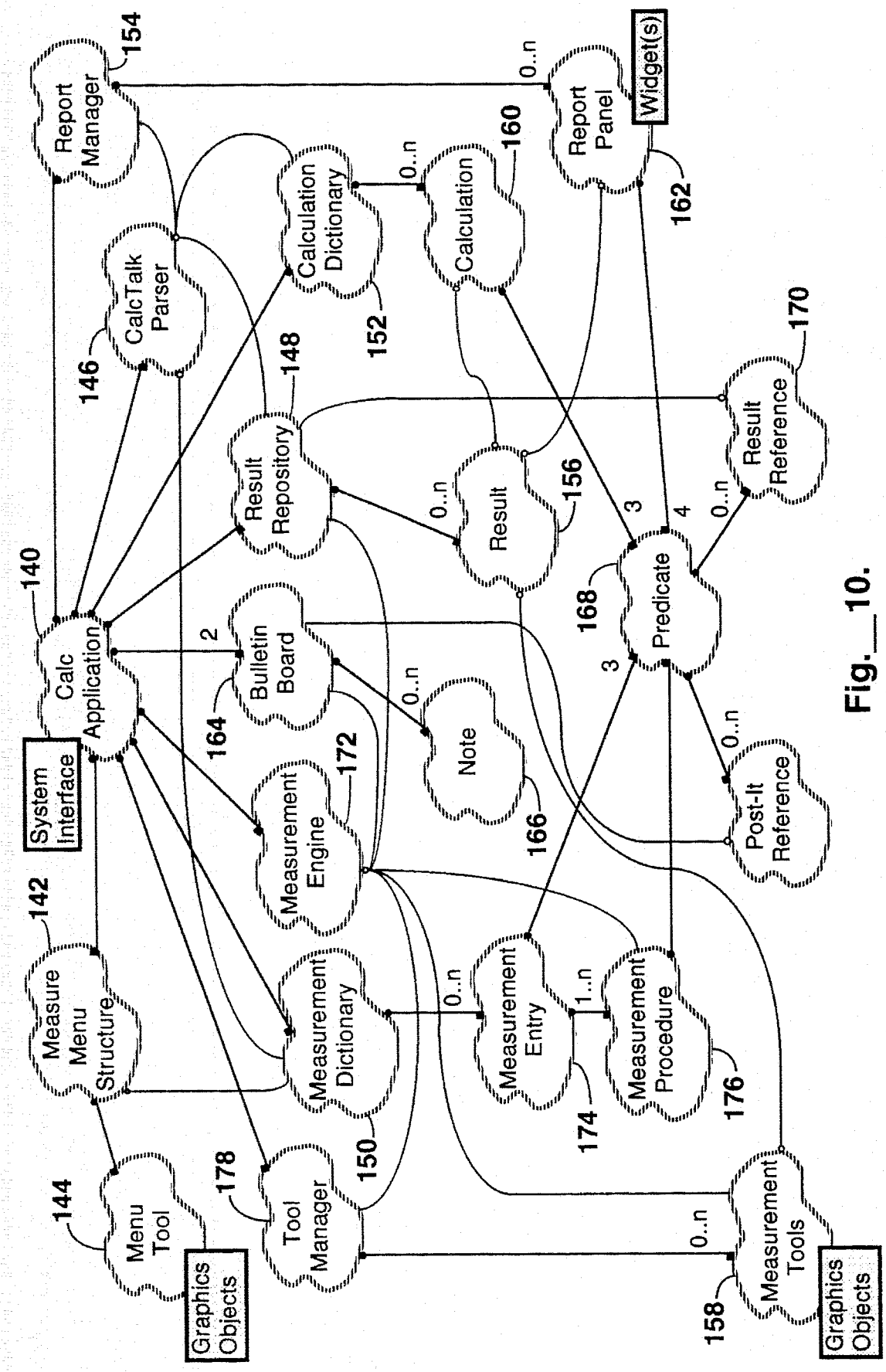
FIG. 10 is a diagram of the software architecture used with a preferred embodiment of the present invention.

FIG. 10 shows the architecture of the CalcApplication and its sub-components. The format of this figure is in the spirit of a Booch class diagram which is a known way of representing objected-oriented systems. The preferred embodiment is written primarily in $C^{++}$, which allows some opportunity for code re-use through class hierarchies. Key base classes are noted, but the complete inheritance hierarchy is not given.

The CalcApplication class 140 is intended to have only one instance. It contains the other major subsystems of the calculation system, coordinates their behavior, and provides their primary interface to the remainder of the ultrasound machine.

The Measure Menu Structure 142 class is also intended to have one instance. It is the software module which maintains the complete menu structure for the Calculation Package and provides access to the Menu Tool 144 through which the user chooses a measurement to perform. The Measure Menu Structure reads the description of the menu structure from a data file on the ultrasound system's hard disk when the System is initialized. The Measure Menu Structure is also responsible for maintaining the user's current location in the Measure Menu Structure between presentations of the Menu.

The Menu Tool 144 is a separate component of software which is responsible for issuing commands to the ultrasound machine's X-Windows server to effect the actual graphical presentation of the menu. Such software components are commonly written by the developers of graphical user interfaces. In the preferred embodiment, the Menu Tool is implemented using the concepts of Motif widgets which have been extended to display the user's previous choices in the menu hierarchy. The user manipulates the menu tool with the ultrasound machine's Trackball and Select Key, whose output is routed to the CalcApplication, then to the Measure Menu Structure, and finally to the Menu Tool.

The CalcTalk Parser 146 class is intended to have one instance. It is the software module which parses Calculation System data files in the CalcTalk language, the current definition of which is given in appendix III. The CalcTalk parser is implemented using lex and yacc, software tools well known to programmers who work in the UNIX environment.

The CalcTalk files, which in the preferred embodiment are stored on the ultrasound machine's hard disk, contain descriptions of 1) the clinical data, called "Results" in this architecture, measured and manipulated by the Calculation System, 2) the procedures, called "Measurements" by which the user measures quantities in the image data, 3) the calculation formulae by which higher order data are derived from measured quantities, and 4) the report definitions by which measured quantities and higher order data are presented in an organized fashion on a full-screen form or printed output. These CalcTalk files describe the contents of the Calculation package; they are read and parsed when the system is initialized. The CalcTalk Parser transmits the definitions of Results, Measurements, Calculations, and Reports to the Result Repository 148, Measurement Dictionary 150, Calculation Dictionary 152, and Report Manager 154, respectively.

The Result Repository 148 class is intended to have one instance, which acts as the database of measured and derived quantities for the Calculation System. The Repository contains the structure of the possible quantification data which the Calculation Package can contain, and it also contains the specific instances of data pertaining to the current exam. Appendix III describes in greater detail the Calculation System's capabilities for organizing and manipulating quantification data; in this preferred embodiment these capabilities are implemented in the Result Repository. There is one instance of the Result 156 class for each piece of quantification data in the Result Repository. Results can be both produced (i.e., have their values set by the output of) and consumed (i.e., have their values serve as input to) by Measurement Tools 158, Calculations 160, and Report Panels 162. Results and their Producers and Consumers can be dynamically configured in a dependency network such that changes to input Results propagate through the network. The data types of Results available, the operators on those data types, and the details of binding Results to the output ports of Producers and the input ports of Consumers are described more fully in the appendix III. The preferred embodiment includes base classes for Result Producers and Result Consumers.

The Bulletin Board 164 class maintains that part of the state of the Calculation System which is not quantification data. It is an entity onto which other components can post an item or a piece of information so that it can be seen or used by other components. System components can also remove posted items. In the original architecture, the posted items are of, or are derived from, class Note 166. For performance reasons, the system is implemented without a Note base class and items are posted directly to the Bulletin Board. There are two Bulletin Board instances in the preferred embodiment: one which maintains the local name space during the execution of a procedure by the Measurement Engine, and the Main Board which maintains posted items across procedures. Posting items as described in the appendix III places them on the Main Board. The CalcApplication posts and removes items from the Main Board to indicate the state of the ultrasound machine.

The Predicate class 168 is intended to have multiple instances. It provides the ability to evaluate a Boolean expression based on the existence of Results 156 in the Result Repository 148 and Notes 166 on the main Bulletin Board 164. Predicates also provide the capability to assign local names to the objects for whose existence they test, items as described in the appendix III.

Predicates contain instances of the Note reference 168 class and the Result Reference 170 class. The former performs a query of the main bulletin board about the existence of a postable note and the latter performs a query of the Result Repository about the existence of a particular Result (or, as described in the in appendix III, a series of Results).

Predicates supply the general mechanism by which Measurements, Measurement Procedures, Calculations, and Reports are sensitive to the state of the Calculation System and the state of the ultrasound machine. Appendix III provides a full description of the CalcTalk syntax for Predicates and a description of each instance of Predicate usage.

The Measurement Dictionary 150 class is intended to have one instance. It is the software module that maintains the definitions of the Measurements by which the user measures quantities in the Image data; these definitions are entered by the CalcTalk Parser 146 during initialization. The Measurement Dictionary provides access to and the status of individual Measurements to the Measure Menu Structure 142 and Measurement Engine 172.

The definition of each entry in the Measurement Dictionary is represented as an instance of the Measurement Entry 174 class. This class has three Predicates: Enable, Select, and Satisfied, which test whether the Measurement may be presented to the user, whether the Measurement has been selected by the user, and whether the outputs of the Measurement already exist, respectively. The details of each Predicate are described in appendix III. The Enable and Select Predicates must evaluate to True for the Measurement to be presented in the menu. If the Satisfied Predicate evaluates to True, the Measurement will still be presented, but the presentation may include an indication that performing the Measurement is not necessary. In the preferred embodiment, this indication is presented as a check mark next to the Measurement name in the menu.

Each instance of a Measurement Entry includes one or more instances of the Measurement Procedure 176 class. Each such instance defines the sequence of steps executed by the Measurement Engine 172 to guide the user through the quantification of some image structure or structures. Each Measurement Procedure includes a Requires Predicate (described fully in the appendix III). If at least one Measurement Procedure for a given Measurement Entry has a Requires Predicate that evaluates to True, the user will be able to select that Measurement when it is presented in the Menu Tool. If none of a given Measurement Entry's Measurement Procedures have Requires Predicates which evaluate to True, the user will not be able to select the corresponding Measurement when it is presented in the Menu Tool. In the preferred embodiment, the Measurements which are not selectable are presented with a grayed out effect, familiar to the developers of graphical user interfaces, to so indicate.

The Measurement Engine 172 class is intended to have one instance. It is the software module that sequences the System through the steps of the procedure by which the user measures some quantity in the image data. The Measurement Engine communicates with the other components of the System and, through the CalcApplication 140, with the ultrasound machine. The Measurement engine is an interpreter optimized to execute the dynamic portions of CalcTalk. Its most frequently used commands include: directing the Tool Manager 178 to create specific tools, directing the Result Repository to create specific Results 156 and attaching the appropriate Results to the appropriate binding sites on the appropriate tools. The details of the Measurement Engine's capabilities are given in the appendix III.

The Tool Manager 178 class is intended to have one instance. It is the software module that manages the creation, use, appearance, and deletion of instances of the Measurement Tools 158 class, which are software modules that effect graphical tools by which the user can measure quantities in the Image data. Typical measurement tools are calipers, ellipses and traces, which are familiar to most users of medical ultrasound imaging equipment. The measurement tools are manipulated by the ultrasound machine's track ball, select key, and soft keys whose output is routed to the CalcApplication, then to the Tool Manager and then to the Tool being manipulated. In the preferred embodiment, the Measurement Tools use software libraries which issue commands to the X-Windows server to execute the necessary graphics commands.

The Calculation Dictionary 152 class is intended to have one instance, which manages the definitions and creation of the actual Calculations 160 in the Calculation System. Calculations are not manipulated by users directly, but instead automatically derive certain quantities from those measured directly. The structure of Calculations is very similar to that of Measurements, and is described fully in the appendix III.

The Report Manager 154 class is intended to have one instance, which manages the sections, instances of the Report Panel 162 class, of the on-screen forms in which the measured and derived quantification data are presented. Each Report Panel will be defined with four Predicates: Enable, Select, Requires, and Uses. The Enable, Select, and Requires Predicates should function similarly to those for Measurements and Calculations. The Uses Predicate will be somewhat different in that it will continue to retrieve Results after it has initially evaluated to True. These Predicates will provide the mechanism by which the Report presents data relevant to the assessment goals indicated by the user through menu selections.

The Report Panel 162 will provides the mechanism for displaying one atomic section, or panel, of the on-screen Calculation System report form. In the preferred embodiment, this class will use Motif and custom widgets, software tools well known to developers of graphical user interfaces.

Various details of the implementation and method are merely illustrative of the invention. It will be understood that the various changes and such details may be within the scope of the invention, which is to be limited only by the appended claims.

APPENDIX I

Basic Measurements
  M-Mode
    Right Ventricle-Left Ventricle M-mode
      Right Ventricle Anterior Wall in diastole and systole
      Right Ventricle in diastole and systole
      Interventricular Septum in diastole and systole
      Left Ventricle in diastole and systole
      Left Ventricle Posterior Wall in diastole and systole
      Pericardial Effusion
    Mitral Valve M-mode
      Mitral Valve DE
      Mitral Valve E-F Slope
      Mitral Valve E-point Septal Separation
    Left Atrium/Aorta M-mode
      Aorta diameter in diastole
      Left Atrium in systole
      Aortic Valve cusp separation
    Tricuspid Valve M-Mode
      Tricuspid Valve D-E Slope
      Tricuspid Valve E-F Slope
    Systolic Time Intervals
      Left Ventricle Pre-ejection Period
      Left Ventricle Ejection Time
      Right Ventricle Pre-ejection Period
      Right Ventricle Ejection Time
  2D chamber dimensions
    Parasternal Long Axis View
      Right Ventricle Anterior Wall in diastole and systole
      Right Ventricle in diastole and systole
      Interventricular Septum in diastole and systole
      Left Ventricle Minor Axis, base in diastole and systole
      Left Ventricle Minor Axis in diastole and systole
      Left Ventricle Posterior Wall in diastole and systole
      Aorta root diameter in diastole and systole
      Aortic sinus in systole
      Aorta (sinotubular junction) in systole
      Ascending Aorta in systole
      Left Atrium Diameter in diastole and systole
      Mitral Valve Annulus in diastole and systole
      Aortic Valve cusp separation
      Left Atrium Area in systole
      Right Atrium Area in diastole and systole
      Right Ventricle Area in diastole and systole
      Tricuspid Valve Annulus in systole
      Superior Vena Cava inspiration, expiration Parasternal Short Axis view, Chordal level
    Right Ventricle Anterior Wall in diastole and systole
    Right Ventricle in diastole and systole
    Interventricular Septum in diastole and systole
    Left Ventricle Posterior Wall in diastole and systole
    Left Ventricle Area in diastole and systole
PARASTERNAL SHORT AXIS, Papillary level
    Right Ventricle Anterior Wall in diastole and systole
    Right Ventricle in diastole and systole
    Interventricular Septum in diastole and systole
    Left Ventricle in diastole and systole
    Left Ventricle Posterior Wall in diastole and systole
    Left Ventricle Area in diastole and systole
PARASTERNAL SHORT AXIS, Aortic Valve Level
    Aorta in diastole and systole
    Left Main Coronary
    Left Circumflex Coronary
    Left Anterior Descending Coronary
    Right Main Coronary
    Left Atrium Diameter in diastole and systole
    Left Atrium Area in diastole and systole
    Right Atrium Area in diastole and systole
    Main Pulmonary Artery in diastole and systole
    Right Pulmonary Artery Diameter in diastole and systole
    Left Pulmonary Artery Diameter in diastole and systole
Apical 4 Chamber View
    Left Ventricle Major Axis in diastole and systole
    Left Ventricle Minor Axis, papillary muscle level in diastole and systole
    Left Ventricle Minor Axis, chordal level in diastole and systole
    Left Ventricle Area in diastole and systole
    Right Ventricle Major Axis in diastole and systole
    Right Ventricle Minor Axis in diastole and systole
    Right Ventricle Area in diastole and systole
    Left Atrium Major Axis in diastole and systole
    Left Atrium Minor Axis in diastole and systole
    Mitral Valve Annulus in diastole
    Left Atrium Area in diastole and systole
    Right Atrium Area in diastole and systole
    Tricuspid Valve Annulus in diastole
    Left upper Pulmonic Valve
    Left lower Pulmonic Valve
    R upper Pulmonic Valve
    R Lower Pulmonic Valve
    Right Atrium Major Axis in diastole and systole
    Right Atrium Minor Axis in diastole and systole
Apical 2 Chamber View
    Left Ventricle Major Axis in diastole and systole
    Left Ventricle Minor Axis, papillary muscle level in diastole and systole
    Left Ventricle Minor Axis, chordal level in diastole and systole
    Left Atrium Area in diastole and systole
    Mitral Valve Annulus Diameter in diastole
    Left Atrium Major Axis in diastole and systole
    Left Atrium Minor Axis in diastole and systole

SSN, Long Axis
    Transverse Aorta Diameter in diastole and systole
    Aorta Isthmus Diameter in diastole and systole
    Descending Aorta Diameter in diastole and systole
    RPA Diameter in diastole and systole
    RPA Area in diastole and systole
SSN, Short Axis
    Transverse Aorta Diameter in diastole and systole
    Transverse Aorta Area in diastole and systole
    Superior Vena Cava Diameter inspiration, expiration
    RPA Diameter in diastole
    LPA Diameter in diastole
    Right upper Pulmonic Valve in diastole and systole
    R Lower Pulmonic Valve in diastole and systole
    Left upper Pulmonic Valve in diastole and systole
    Left lower Pulmonic Valve in diastole and systole
2D Volumes
Left Ventricle Volumes
   Apical 4 Chamber View
       Left Ventricle Area in diastole and systole
       Left Ventricle Major Axis in diastole and systole
       Left Ventricle Minor Axis in diastole and systole
   Apical 2 Chamber View
       Left Ventricle Area in diastole and systole
       Left Ventricle Major Axis in diastole and systole
       Left Ventricle Minor Axis in diastole and systole
   Parasternal Short Axis
       Left Ventricle Area, papillary muscle level in diastole and systole
       Left Ventricle Minor Axis, papillary muscle level in diastole and systole
       Right Ventricle Volume
       Right Ventricle Area in diastole and systole
       Right Ventricle Major Axis in diastole and systole
       Right Ventricle Inflow Tract Area in diastole and systole
       Right Ventricle Outflow Tract Area in diastole and systole
Left Atrium Volumes
   View 1
       Left Atrium Area in diastole and systole
   View 2
       Left Atrium Area in diastole and systole
Right Atrium Volumes
   View 1
       Right Atrium Area in diastole and systole
   View 2
       Right Atrium Area in diastole and systole
2D mass
   Left Ventricle mass, Area Length
       Left Ventricle epicardial Area in diastole
       Left Ventricle endocardial Area in diastole
       Left Ventricle Major Axis in diastole
   Left Ventricle mass, Truncated Ellipsoid
       Left Ventricle epicardial Area in diastole
       Left Ventricle endocardial Area in diastole
       Left Ventricle area, Apical 4 Chamber view in diastole
       Left Ventricle Major Axis in diastole Left Ventricle Semi-major Axis
　　　　Left Ventricle Truncated Semi-Major Axis
　　　　Left Ventricle Minor Axis
Basic Doppler
　Aortic Valve
　　　　Aortic Valve Peak Velocity
　　　　Aortic Valve Mean Velocity
　　　　Aortic Valve Peak Gradient
　　　　Aortic Valve Velocity Time Integral
　Pulmonic Valve
　　　　Pulmonic Valve Peak Velocity
　　　　Pulmonic Valve Mean Velocity
　　　　Pulmonic Valve Peak Gradient
　　　　Pulmonic Valve Velocity Time Integral
　Mitral Valve
　　　　Mitral Valve Peak Velocity
　　　　Mitral Valve Mean Gradient
　　　　Mitral Valve Velocity Time Integral
　Tricuspid Valve
　　　　Tricuspid Valve Peak Velocity
　　　　Tricuspid Valve Velocity Time Integral
　　　　Tricuspid Valve Mean Gradient
　Venous Flow
　　　　Superior Vena Cava Peak Velocity
　　　　Inferior Vena Cava Peak Velocity
　　　　Right Upper Pulmonary Vein Peak Velocity
　　　　Right Lower Pulmonary Vein Peak Velocity
　　　　Left Upper Pulmonary Vein Peak Velocity
　　　　Let Lower Pulmonary Vein Peak Velocity

Doppler Pressure Predictions
Right Ventricle Systolic Pressure via Tricuspid Regurgitation
    Tricuspid Regurgitation Peak Velocity
    Tricuspid Regurgitation Peak Gradient
    Right Atrium Pressure (entered)
    Ventricular Septal Defect Peak Velocity
    Ventricular Septal Defect Peak Gradient
    Systolic Blood Pressure
Pulmonary Artery Diastolic Pressure
    Pulmonary Regurgitation Peak Velocity
    Pulmonary Regurgitation Peak Gradient
    Right Atrium Pressure (entered)
Left Ventricle Systolic Pressure
    Aortic Valve Peak Velocity
    Aortic Valve Peak Gradient
    Systolic Blood Pressure
Left Ventricle End-Diastolic Pressure
    Aortic Regurgitation end diastolic velocity
    Aortic Regurgitation end diastolic gradient
    Diastolic Blood Pressure
Left Atrial Systolic Pressure
    Mitral Regurgitation Peak Velocity
    Mitral Regurgitation Peak grad.
    Systolic Blood Pressure
Simple Bernoulli (user-named)
    V2 (Trans-orifice) Peak Velocity
    V2 (Trans-orifice) Peak Gradient
Expanded Bernoulli (user-named)
    V1 (Pre-orifice) Peak Velocity
    V1 (Pre-orifice) Peak Gradient
    V2 (Trans-orifice) Peak Velocity
    V2 (Trans-orifice) Peak Gradient

Valve Stenosis
Aortic Valve
M-Mode
Interventricular Septum inspiration, expiration
Left Ventricle in diastole and systole
Left Ventricle Posterior Wall in diastole and systole
2D
Left Ventricle mass, Area Length
Left Ventricle epicardial Area in diastole
Left Ventricle endocardial Area in diastole
Left Ventricle Major Axis in diastole
Left Ventricle mass, Truncated Ellipsoid
Left Ventricle epicardial Area in diastole
Left Ventricle endocardial Area in diastole
Left Ventricle area, Apical 4 Chamber view in diastole
Left Ventricle Major Axis in diastole
Left Ventricle Semi-major Axis
Left Ventricle Truncated Semi-Major Axis
Left Ventricle Minor Axis
Aortic Doppler
Aortic Valve Peak Velocity
Aortic Valve Peak Gradient
Aortic Valve Velocity Time Integral
Aortic Valve Mean Gradient
Aortic Valve Acceleration Time
Aortic Valve Ejection Time
Aortic Valve Continuity Equation
Aortic Valve Peak Velocity
Aortic Valve Velocity Time Integral
Aortic Valve Mean Gradient
Aortic Valve Mean Acceleration
Aortic Valve Acceleration Time
Aortic Valve Ejection Time
Left Ventricle Outflow Tract Peak Velocity
Left Ventricle Outflow Tract Velocity Time Integral
Left Ventricle Outflow Tract Mean Velocity
Left Ventricle Outflow Tract Mean Gradient
Left Ventricle Outflow Tract Diameter
Proximal Isovelocity Surface Area method Aortic Valve
Aortic Valve Proximal Isovelocity Surface Area Radius
Aortic Valve Proximal Isovelocity Surface Area Radius Velocity
Aortic Valve Peak Velocity
Aortic Valve Velocity Time Integral
Aortic Valve Mean Velocity
Aortic Valve Mean Gradient
Aortic Valve Mean Acceleration
Aortic Valve Acceleration Time
Aortic Valve Ejection Time
Aortic Valve Proximal Isovelocity Surface Area
Aortic Valve Peak flow Pulmonary Valve
  Pulmonic Valve Doppler
    Pulmonic Valve Peak Velocity
    Pulmonic Valve Peak Gradient
    Pulmonic Valve Velocity Time Integral
    Pulmonic Valve Mean Velocity
    Pulmonic Valve Mean Gradient
    Pulmonic Valve Acceleration Time
    Pulmonic Valve Ejection Time
  Pulmonic Valve Continuity Equation
    Pulmonic Valve Peak Velocity
    Pulmonic Valve Velocity Time Integral
    Pulmonic Valve Mean Gradient
    Pulmonic Valve Mean Acceleration
    Pulmonic Valve Acceleration Time
    Pulmonic Valve Ejection Time
    Right Ventricle Outflow Tract Peak Velocity
    Right Ventricle Outflow Tract Velocity Time Integral
    Right Ventricle Outflow Tract Mean Velocity
    Right Ventricle Outflow Tract Peak Gradient
    Right Ventricle Outflow Tract Diameter
  Proximal Isovelocity Surface Area Method Pulmonic Valve
    Pulmonic Valve Proximal Isovelocity Surface Area radius
    Pulmonic Valve Proximal Isovelocity Surface Area radius velocity
    Pulmonic Valve Peak Velocity
    Pulmonic Valve Velocity Time Integral
    Pulmonic Valve Mean Velocity
    Pulmonic Valve Mean Gradient
    Pulmonic Valve Mean Acceleration
    Pulmonic Valve Acceleration Time
    Pulmonic Valve Ejection Time
    Pulmonic Valve Proximal Isovelocity Surface Area
Mitral Valve
  Mitral Valve 2D Measurements
    Mitral Valve Area
    Mitral Valve Anterior-Posterior Diameter
    Mitral Valve Medial-Lateral Diameter
  Mitral Valve Continuity Equation
    Mitral Valve Proximal Velocity Time Integral
    Mitral Valve Proximal Diameter
    Mitral Valve Proximal Area
    Mitral Valve Peak Velocity
    Mitral Valve Velocity Time Integral
    Mitral Valve Mean Gradient
  Mitral Valve Doppler
    Mitral Valve Peak Velocity
    Mitral Valve Velocity Time Integral
    Mitral Valve Mean Gradient
    Mitral Valve Pressure Half-Time
    Mitral Valve Deceleration Time Proximal Isovelocity Surface Area Method Mitral Valve
        Mitral Valve Proximal Isovelocity Surface Area Radius
        Mitral Valve Aliasing Velocity
        Mitral Valve Proximal Isovelocity Surface Area Funnel Angle
        Mitral Valve Peak Velocity
        Mitral Valve Velocity Time Integral
        Mitral Valve Mean Gradient
        Mitral Valve Proximal Isovelocity Surface Area
Tricuspid Valve
  2D Measurements
        Tricuspid Valve Area (by planimetry)
        Tricuspid Valve Diameter (Anterior-Posterior)
        Tricuspid Valve Diameter (Medial-Lateral)
    Tricuspid Valve Continuity Equation
        Proximal Velocity Time Integral
        Proximal Diameter
        Tricuspid Valve Peak Velocity
        Tricuspid Valve Velocity Time Integral
        Tricuspid Valve Mean Gradient
        Tricuspid Valve Doppler
        Tricuspid Valve Peak Velocity
        Tricuspid Valve Velocity Time Integral
        Tricuspid Valve Mean Gradient
        Tricuspid Valve Pressure Half-Time
        Tricuspid Valve Deceleration Time
    Proximal Isovelocity Surface Area Method Tricuspid Valve
        Color Doppler Imaging Radius
        Aliasing Velocity
        Color Doppler Imaging Funnel Angle
        Tricuspid Valve Peak Velocity
        Tricuspid Valve Velocity Time Integral
        Tricuspid Valve Mean Gradient
        Tricuspid Valve Proximal Isovelocity Surface Area
    [Site] Proximal Isovelocity Surface Area Method
        [Site]Color Doppler Imaging Radius
        [Site]Aliasing Velocity
        [Site]Color Doppler Imaging Funnel Angle
        [Site] Peak Velocity
        [Site] Velocity Time Integral
        [Site] Mean Gradient
        [Site] Proximal Isovelocity Surface Area

Valve Regurgitation
Aortic Valve
M-Mode
Left Ventricle in diastole and systole
2D
Left Ventricle Dimensions
PARASTERNAL LONG AXIS
Left Ventricle Minor Axis in diastole and systole
PARASTERNAL SHORT AXIS, Papillary muscle level
Left Ventricle Area, papillary muscle level in diastole and systole
Left Ventricle Minor Axis, papillary muscle level in diastole and systole
Apical 4 Chamber View
Left Ventricle Major Axis in diastole and systole
Left Ventricle Minor Axis, papillary muscle level in diastole and systole
Left Ventricle Minor Axis, chordal level in diastole and systole
Left Ventricle Area in diastole and systole
Apical 2 Chamber View
Left Ventricle Major Axis in diastole and systole
Left Ventricle Minor Axis, papillary muscle level in diastole and systole
Left Ventricle Minor Axis, chordal level in diastole and systole
Left Ventricle Area in diastole and systole
Left Ventricle mass, Area Length
Left Ventricle epicardial Area in diastole
Left Ventricle endocardial Area in diastole
Left Ventricle Major Axis in diastole
Left Ventricle mass, Truncated Ellipsoid
Left Ventricle epicardial Area in diastole
Left Ventricle endocardial Area in diastole
Left Ventricle area, apical 4 chamber view in diastole
Left Ventricle Major Axis in diastole
Left Ventricle Semi-major Axis
Left Ventricle Truncated Semi-Major Axis
Left Ventricle Minor Axis
Aortic Regurgitation CD Jet Ratios
Aortic Regurgitation Jet Height
Left Ventricle Outflow Tract Height
Aortic Regurgitation Jet Area
Aortic Regurgitation Slope
Aortic Regurgitation Slope
Aortic Regurgitation Deceleration Time
Aortic Regurgitation Velocity Half-Time
Aortic Regurgitation Pressure Half-Time
Aortic Regurgitation Proximal Isovelocity Surface Area Method
Proximal Isovelocity Surface Area Radius
Aortic Regurgitation Aliasing Velocity
Aortic Regurgitation Velocity Time Integral
Aortic Regurgitation Volume by Doppler/Doppler
Aortic Valve Velocity Time Integral
Aortic Valve Mean Velocity
Left Ventricle Outflow Tract Diameter in systole
Right Ventricle Outflow Tract Diameter in systole
Pulmonic Valve Velocity Time Integral
Pulmonic Valve Mean Velocity

Aortic Regurgitation Volume by 2D/Doppler
  Apical 4 Chamber View
    Left Ventricle Area in diastole and systole
    Left Ventricle Major Axis in diastole and systole
    Left Ventricle Minor Axis, base in diastole and systole
  Apical 2 Chamber View
    Left Ventricle Area in diastole and systole
    Left Ventricle Major Axis in diastole and systole
    Left Ventricle Minor Axis in diastole and systole
  Pulmonic Valve Doppler
    Pulmonic Valve Peak Velocity
    Pulmonic Valve Velocity Time Integral
    Pulmonic Valve Mean Gradient
    Pulmonic Valve Mean Acceleration
    Pulmonic Valve Diameter
Aortic Regurgitation by 2D/2D
  Apical 4 Chamber View
    Left Ventricle Area in diastole and systole
    Left Ventricle Major Axis in diastole and systole
    Left Ventricle Minor Axis, base in diastole and systole
  Apical 2 Chamber View
    Left Ventricle Area in diastole and systole
    Left Ventricle Major Axis in diastole and systole
    Left Ventricle Minor Axis in diastole and systole
  Right Ventricle
    Right Ventricle Area in diastole and systole
    Right Ventricle Major Axis in diastole and systole
Mitral Valve
M-Mode
    Left Ventricle in diastole and systole
    Left Atrium in systole
2D
  Left Atrium Volumes
    View 1
      Left Atrium Area in diastole and systole
    View 2
      Left Atrium Area in diastole and systole
  Left Ventricle Volumes
    Apical 4 Chamber View
      Left Ventricle Area in diastole and systole
      Left Ventricle Major Axis in diastole and systole
      Left Ventricle Minor Axis in diastole and systole
    Apical 2 Chamber View
      Left Ventricle Area in diastole and systole
      Left Ventricle Major Axis in diastole and systole
      Left Ventricle Minor Axis in diastole and systole
  PARASTERNAL SHORT AXIS
    Left Ventricle Area, papillary muscle level in diastole and systole
    Left Ventricle Minor Axis, papillary muscle level in diastole and systole
  Mitral Regurgitation Proximal Isovelocity Surface Area Method
    Proximal Isovelocity Surface Area Radius
    Aliasing Velocity
    Mitral Regurgitation Peak Velocity
    Mitral Regurgitation Velocity Time Integral

Mitral Regurgitation by 2D/Doppler
  Apical 4 Chamber View
    Left Ventricle Area in diastole and systole
    Left Ventricle Major Axis in diastole and systole
    Left Ventricle Minor Axis in diastole and systole
  Apical 2 Chamber View
    Left Ventricle Area in diastole and systole
    Left Ventricle Major Axis in diastole and systole
    Left Ventricle Minor Axis in diastole and systole
    Left Ventricle Outflow Tract Velocity Time Integral
    Left Ventricle Outflow Tract Diameter
Mitral Regurgitation by 2D/2D
  Apical 4 Chamber View
    Left Ventricle Major Axis in diastole and systole
    Left Ventricle Minor Axis, base in diastole and systole
    Left Ventricle Area in diastole and systole
  Apical 2 Chamber View
    Left Ventricle Minor Axis in diastole and systole
    Left Ventricle Minor Axis in diastole and systole
    Left Ventricle Area in diastole and systole
    Right Ventricle Area in diastole and systole
    Right Ventricle Major Axis in diastole and systole
Tricuspid Valve
 M-Mode
    Right Ventricle Anterior Wall in diastole
 2 D
  Right Ventricle Volume
    Right Ventricle Area in diastole and systole
    Right Ventricle Major Axis in diastole and systole
    Right Ventricle Inflow Tract Area in diastole and systole
    Right Ventricle Outflow Tract Area in diastole and systole
  Right Atrium Volume
   View 1
    Right Atrium Area in diastole and systole
   View 2
    Right Atrium Area in diastole and systole
Tricuspid Regurgitation by Proximal Isovelocity Surface Area Method
    Color Doppler Imaging Radius
    Aliasing Velocity
Tricuspid Regurgitation by 2D/Doppler
    Right Ventricle Area, method in diastole and systole
    Right Ventricle Major Axis in diastole and systole
    Right Ventricle Outflow Tract Velocity Time Integral
    Right Ventricle Outflow Tract Diameter
Tricuspid Regurgitation by 2D/2D
  Apical 4 Chamber View
    Left Ventricle Area in diastole and systole
    Left Ventricle Major Axis in diastole and systole
    Left Ventricle Minor Axis, base in diastole and systole
  Apical 2 Chamber View
    Left Ventricle Area in diastole and systole
    Left Ventricle Major Axis in diastole and systole
    Left Ventricle Minor Axis in diastole and systole
    Right Ventricle Area in diastole and systole Right Ventricle Major Axis in diastole and systole
Pulmonic Valve
  M-Mode
        Right Ventricle in diastole and systole
  2D
        Right Ventricle Volume
        Right Ventricle Area in diastole and systole
        Right Ventricle Major Axis in diastole and systole
        Right Ventricle Inflow Tract Area in diastole and systole
        Right Ventricle Outflow Tract Area in diastole and systole
Pulmonic Regurgitation by Proximal Isovelocity Surface Area Method
    Color Doppler Imaging Radius
    Aliasing Velocity
    Pulmonic Regurgitation Velocity Time Integral
Pulmonic Regurgitation by Doppler/Doppler
    Aortic Valve Velocity Time Integral
    Pulmonic Valve Velocity Time Integral
    Left Ventricle Outflow Tract Diameter
    Right Ventricle Outflow Tract Diameter
Pulmonic Regurgitation by 2D/Doppler
    Right Ventricle Area in diastole and systole
    Right Ventricle Major Axis in diastole and systole
    Aortic Valve Peak Velocity
    Aortic Valve Velocity Time Integral
    Aortic Valve Mean Gradient
    Aortic Valve Mean Acceleration
    Left Ventricle Outflow Tract Diameter
Pulmonic Regurgitation by 2D/2D
  Left Ventricle
    Apical 4 Chamber View
      Left Ventricle Area in diastole and systole
      Left Ventricle Major Axis in diastole and systole
      Left Ventricle Minor Axis, base in diastole and systole
    Apical 2 Chamber View
      Left Ventricle Area in diastole and systole
      Left Ventricle Minor Axis in diastole and systole
      Left Ventricle Minor Axis in diastole and systole
  Right Ventricle
    Right Ventricle Area in diastole and systole
    Right Ventricle Major Axis in diastole and systole
    Right Ventricle Inflow Tract Area in diastole and systole
    Right Ventricle Outflow Tract Area in diastole and systole
[SITE] Proximal Isovelocity Surface Area Method
    [SITE] Color Doppler Imaging Radius
    [SITE] Aliasing Velocity
    [SITE] Velocity Time Integral Shunts
  Left Ventricle Outflow Tract Cardiac Output
    Left Ventricle Outflow Tract Velocity Time Integral
    Left Ventricle Outflow Tract Diameter
  Pulmonic Valve Doppler
    Right Ventricle Outflow Tract Velocity Time Integral
    Right Ventricle Outflow Tract Diameter
  Qp (pulmonary side flow)/Qs (systemic side flow)
    Pulmonic side Velocity Time Integral
    Pulmonic side Diameter
    Systemic side Velocity Time Integral
    Systemic side Diameter

Ventricular Function
Systolic Function
Left Ventricle Systolic Function
M-mode
- Left Ventricle Diameter in diastole and systole
- Mitral Valve E-point Septal Separation
- Left Ventricle Ejection Time
- Left Ventricle Posterior Wall in diastole
- Left Ventricle Major Axis in systole

2D
PARASTERNAL SHORT AXIS
- Left Ventricle Minor Axis, chordal level in diastole and systole
- Left Ventricle Minor Axis, papillary muscle level in diastole and systole
- Left Ventricle Area, papillary muscle level in diastole and systole

Apical 4 Chamber View
- Left Ventricle Area in diastole and systole
- Left Ventricle Major Axis in diastole and systole
- Left Ventricle Minor Axis in diastole and systole

Apical 2 Chamber View
- Left Ventricle Area in diastole and systole
- Left Ventricle Major Axis in diastole and systole
- Left Ventricle Minor Axis in diastole and systole

Doppler
- Mitral Regurgitation Slope
- Aortic Valve Mean Acceleration
- Aortic Valve Acceleration Time
- Aortic Valve Ejection Time

Right Ventricle Systolic Function
2D
- Right Ventricle Area in diastole and systole
- Right Ventricle Major Axis in diastole and systole
- Right Ventricle Inflow Tract Area in diastole and systole
- Right Ventricle Outflow Tract Area in diastole and systole

Doppler
- Tricuspid Regurgitation Slope
- Pulmonic Valve Mean Acceleration
- Pulmonic Valve Acceleration Time
- Pulmonic Valve Ejection Time

Diastolic Function
Left Ventricle
- Mitral Valve Peak Velocity
- Mitral Valve E Peak Velocity
- Mitral Valve A Peak Velocity
- Mitral Valve Deceleration Time
- Mitral Valve A Duration
- Left Ventricle Isovolumic Relaxation Time

Pulmonary Venous Flow
- Pulmonary Vein S Peak Velocity
- Pulmonary Vein D Peak Velocity
- Pulmonary Vein a Peak Velocity
- Pulmonary Vein D Velocity Time Integral
- Pulmonary Vein S Velocity Time Integral
- Pulmonary Vein Duration D Pulmonary Vein a duration  
    Mitral A duration  
Right Ventricle  
    Tricuspid Valve Peak Velocity  
    Tricuspid Valve E Peak Velocity  
    Tricuspid Valve A Peak Velocity  
    Tricuspid Valve E Deceleration Time  
    Tricuspid Valve A Duration  
    Right Ventricle Isovolumic Relaxation Time  
Respiration Trends  
    Left Ventricle Isovolumic Relaxation Time, inspiration  
    Left Ventricle Isovolumic Relaxation Time, expiration.  
    Mitral Valve Deceleration Time  
    Mitral Valve E Peak Velocity inspiration  
    Mitral Valve E Peak Velocity expiration  
    Mitral Valve A Peak Velocity inspiration  
    Mitral Valve A Peak Velocity expiration  
    Superior Vena Cava, inspiration  
    Inferior Vena Cava, inspiration  
    Superior Vena Cava Peak Velocity, inspiration  
    Superior Vena Cava Peak Velocity, expiration  
    Inferior Vena Cava Peak Velocity, inspiration  
    Inferior Vena Cava Peak Velocity, expiration

APPENDIX II

1. Aortic sino-tubular junction/ Aortic root ratio
2. Aortic Valve area, Continuity Equation (Mean Gradient method)
3. Aortic Valve area, Continuity Equation (Peak Velocity method)
4. Aortic Valve area, Continuity Equation (Velocity Time Integral method)
5. Aortic Valve Area index (Body Surface Area) (Proximal Isovelocity Surface Area method)
6. Aortic Valve area Index, Continuity Equation, (Mean Gradient method)
7. Aortic Valve area Index, Continuity Equation, (Peak Velocity method)
8. Aortic Valve area Index, Continuity Equation, (Velocity Time Integral method)
9. Aortic Valve Area (Proximal Isovelocity Surface Area method)
10. Aortic Valve Acceleration Time/Ejection Time
11. Aortic Valve Cardiac Index
12. Aortic Valve Cardiac Output
13. Aortic Valve Cardiac Output, (Proximal Isovelocity Surface Area method)
14. Aortic Valve Cardiac Index (Proximal Isovelocity Surface Area method)
15. Aortic Valve Stroke Index
16. Aortic Valve Stroke Index (Proximal Isovelocity Surface Area method)
17. Aortic Valve Stroke Volume
18. Aortic Valve Stroke Volume (Proximal Isovelocity Surface Area method)
19. Aortic Regurgitation Effective Regurgitant Orifice
20. Aortic Regurgitation Jet Height/Left Ventricular Outflow Tract Height ratio
21. Aortic Regurgitation Regurgitant Fraction
22. Aortic Regurgitation Volume (2D/2D)
23. Aortic Regurgitation Volume
24. Aortic Regurgitation Volume
25. Aortic Regurgitation Volume
26. Cardiac Index, Area/Length method Biplane
27. Cardiac Index (M-mode)
28. Cardiac Index, Qp / Qs (systemic flow)
29. Cardiac Output
30. Cardiac Output, Area/Length method Biplane
31. Cardiac Output (M-mode)
32. Circumferential Wall Stress
33. E-point Septal Separation / Left Ventricular End Diastolic Dimension
34. % Fractional shortening, M-mode
35. % Fractional shortening, Parasternal long-axis view
36. % Fractional shortening, Parasternal short-axis view chordal level 37. Isovolumic Relaxation time ratio, inspiration/expiration
38. Inferior Vena Cava inspiration/expiration, Parasternal long-axis view
39. Inferior Vena Cava Peak Gradient
40. Inferior Vena Cava Peak Velocity, inspiration/expiration
41. % Interventricular septum thickening, Parasternal long-axis view
42. % Interventricular septum thickening, Parasternal short-axis view chordal level
43. % Interventricular septum thickening, Parasternal short-axis view papillary muscle level
44. % Interventricular septum thickening
45. Interventricular septum / Left Ventricular posterior wall ratio
46. Interventricular septum / Left Ventricular posterior wall ratio, Parasternal long-axis view
47. Interventricular septum / Left Ventricular posterior wall ratio, Parasternal short-axis view chordal level
48. Interventricular septum / Left Ventricular posterior wall ratio, Parasternal short-axis view papillary muscle level
49. Left Atrium fractional area change
50. Left Atrium systolic pressure
51. Left Atrium Volume, Area/Length method in diastole
52. Left Atrium Volume, Area/Length method in systole
53. Left Atrium Volume in diastole, view 1
54. Left Atrium Volume in diastole, view 2
55. Left Atrium Volume, Method of Discs Biplane in diastole
56. Left Atrium Volume, Method of Discs Biplane in systole
57. Left Atrium Volume in systole, view 1
58. Left Atrium Volume in systole, view 2
59. Left Atrium / Aorta ratio
60. Left ventricular ejection time, corrected
61. Left ventricular preejection period, corrected
62. Left main Coronary Artery / Aorta in diastole
63. % Left Ventricle area change, Parasternal short-axis view chordal level
64. % Left Ventricle area change, Parasternal short-axis view papillary muscle level
65. Left Ventricle Area/Length volume in diastole, Apical 2 chamber view
66. Left Ventricle Area/Length volume in systole, Apical 2 chamber view
67. Left Ventricle Bullet cardiac index
68. Left Ventricle Bullet Cardiac Output
69. Left Ventricle Bullet volume in diastole
70. Left Ventricle Bullet volume in systole
71. Left Ventricle Cardiac Index, Apical 2 chamber view, Area/Length method
72. Left Ventricle Cardiac Index, Apical 2 chamber view, Method of Discs
73. Left Ventricle Cardiac Index, Apical 4 chamber view, Area/Length method
74. Left Ventricle Cardiac Index, Apical 4 chamber view, Method of Discs
75. Left Ventricle Cardiac Index, Biplane Method of Discs 76. Left Ventricle Cardiac Output, Apical 2 chamber view, Area/Length method
77. Left Ventricle Cardiac Output, Apical 2 chamber view, Method of Discs
78. Left Ventricle Cardiac Output, Apical 4 chamber view, Area/Length method
79. Left Ventricle Cardiac Output, Apical 4 chamber view, Method of Discs
80. Left Ventricle Cardiac Output, Biplane Method of Discs
81. Left Ventricle Ejection Fraction, Apical 2 chamber view, Area/Length method
82. Left Ventricle Ejection Fraction, Apical 2 chamber view, Method of Discs
83. Left Ventricle Ejection Fraction, Apical 4 chamber view, Area/Length method
84. Left Ventricle Ejection Fraction, Apical 4 chamber view, Method of Discs
85. Left Ventricle Ejection Fraction, Area/Length method Biplane
86. Left Ventricle Ejection Fraction, Biplane Method of Discs
87. Left Ventricle Ejection Fraction, Bullet
88. Left Ventricle Ejection Fraction (M-mode)
89. Left Ventricle end diastolic pressure
90. Left Ventricle fractional area change
91. % Left Ventricle Fractional shortening, Parasternal long-axis view chordal level
92. % Left Ventricle Fractional shortening, Parasternal short-axis view papillary muscle level
93. Left Ventricle mass, Area Length in diastole
94. Left Ventricle mass, Area Length in diastole, Index (Body Surface Area)
95. Left Ventricle mass, Area Length in diastole, Index (height)
96. Left Ventricle mass, American Society of Echocardiography standard
97. Left Ventricle mass, American Society of Echocardiography standard, corrected
98. Left Ventricle mass, American Society of Echocardiography standard, Corrected Index (Body Surface Area)
99. Left Ventricle mass, American Society of Echocardiography standard, Corrected Index (height)
100. Left Ventricle mass, American Society of Echocardiography standard, Index (Body Surface Area)
101. Left Ventricle mass, American Society of Echocardiography standard, Index (height)
102. Left Ventricle mass, Truncated Ellipse method
103. Left Ventricle mass, Truncated Ellipse method, Index (Body Surface Area)
104. Left Ventricle mass, Truncated Ellipse method, Index (height)
105. Left Ventricle mean wall thickness in diastole
106. Left Ventricle minor radius in diastole, Parasternal short-axis view papillary muscle level
107. Left Ventricle Stroke Index, Area/Length method Biplane
108. Left Ventricle Stroke Index, Biplane Method of Discs
109. Left Ventricle Stroke Index, Bullet
110. Left Ventricle Stroke Index, M-mode
111. Left Ventricle Stroke Volume, Apical 2 chamber view, Area/Length method
112. Left Ventricle Stroke Volume, Apical 2 chamber view, Method of Discs
113. Left Ventricle Stroke Volume, Apical 4 chamber view, Area/Length method 114. Left Ventricle Stroke Volume, Apical 4 chamber view, Method of Discs
115. Left Ventricle Stroke Volume, Area/Length method Biplane
116. Left Ventricle Stroke Volume, Biplane Method of Discs
117. Left Ventricle Stroke Volume, Bullet
118. Left Ventricle Stroke Volume, M-mode
119. Left Ventricle systolic pressure
120. Left Ventricle volume, Area / Length method Biplane in diastole
121. Left Ventricle volume, Area / Length method Biplane in systole
122. Left Ventricle volume, Biplane Method of Discs in diastole
123. Left Ventricle volume, Biplane Method of Discs in systole
124. Left Ventricle Volume in diastole, Apical 2 chamber view
125. Left Ventricle Volume in diastole, Apical 4 chamber view
126. Left Ventricle Volume in systole, Apical 2 chamber view
127. Left Ventricle Volume in systole, Apical 4 chamber view
128. Left Ventricular Outflow Tract Area
129. Left Ventricular Outflow Tract Cardiac Index
130. Left Ventricular Outflow Tract Cardiac Output
131. Left Ventricular Outflow Tract Jet Area
132. Left Ventricular Outflow Tract Stroke Index
133. Left Ventricular Outflow Tract Stroke Volume
134. Left Ventricle Pre-ejection period / Ejection Time
135. % Left Ventricular posterior wall thickening, Parasternal long-axis view
136. % Left Ventricular posterior wall thickening, Parasternal short-axis view chordal level
137. % Left Ventricular posterior wall thickening, Parasternal short-axis view papillary muscle level
138. % Left Ventricular posterior wall thickening, M-Mode
139. Mean Circumferential shortening velocity, Parasternal short-axis view chordal level
140. Mean Velocity of circumferential shortening
141. Mean Velocity of circumferential shortening, 2D parasternal long axis view
142. Mean Velocity of circumferential shortening, corrected
143. Mitral Regurgitation dP/dt
144. Mitral Regurgitation Effective Regurgitant Orifice
145. Mitral Regurgitation Regurgitant Fraction
146. Mitral Regurgitation Regurgitant Fraction, 2D/Doppler
147. Mitral Regurgitation Regurgitant Volume, 2D/Doppler
148. Mitral Regurgitation regurgitant volume, Proximal Isovelocity Surface Area method
149. Mitral Regurgitation Volume (2D/2D)
150. Mitral Valve A/E (velocity method)
151. Mitral Valve A/E (velocity method) expiration
152. Mitral Valve A/E (velocity method) inspiration
153. Mitral Valve A/Pulmonic Valve a duration ratio 154. Mitral Valve annulus area (Biplane Ellipse)
155. Mitral Valve Area, Continuity equation (Velocity Time Integral method)
156. Mitral Valve Area Index, Continuity equation
157. Mitral Valve Area Index, Proximal Isovelocity Surface Area method
158. Mitral Valve Area (Pressure half-time)
159. Mitral Valve Area, Proximal Isovelocity Surface Area method
160. Mitral Valve Cardiac Index, Proximal Isovelocity Surface Area method
161. Mitral Valve Cardiac Output, Proximal Isovelocity Surface Area method
162. Mitral Valve E/A (velocity method)
163. Mitral Valve E/A (velocity method) expiration
164. Mitral Valve E/A (velocity method) inspiration
165. Mitral Valve Peak Flow, Proximal Isovelocity Surface Area method
166. Mitral Valve Peak Gradient
167. Mitral Valve Peak flow rate / Stroke Volume
168. Mitral Valve Stroke Index, Proximal Isovelocity Surface Area method
169. Mitral Valve Stroke Volume, Proximal Isovelocity Surface Area method
170. Pulmonic Regurgitation Effective Regurgitant Orifice
171. Pulmonic Regurgitation Regurgitant Fraction
172. Pulmonic Regurgitation Regurgitant Fraction
173. Pulmonic Regurgitation Regurgitant Volume, Proximal Isovelocity Surface Area method
174. Pulmonic Regurgitation Volume (2D/2D)
175. Pulmonic Regurgitation Volume, 2D/Doppler
176. Pulmonic Regurgitation Volume in Doppler /Doppler
177. Pulmonary artery diastolic pressure
178. Pulmonic Valve area, Continuity Equation (Mean Gradient method)
179. Pulmonic Valve area, Continuity Equation (Peak Velocity method)
180. Pulmonic Valve area, Continuity Equation (Velocity Time Integral method)
181. Pulmonic Valve Area index (Body Surface Area) ( Proximal Isovelocity Surface Area method)
182. Pulmonic Valve area Index, Continuity Equation, (Mean Gradient method)
183. Pulmonic Valve area Index, Continuity Equation, (Peak Velocity method)
184. Pulmonic Valve area Index, Continuity Equation, (Velocity Time Integral method)
185. Pulmonic Valve area (Proximal Isovelocity Surface Area method)
186. Pulmonic Valve Acceleration Time / Ejection Time
187. Pulmonic Valve Cardiac Index
188. Pulmonic Valve Cardiac Output
189. Pulmonic Valve Cardiac Output, Proximal Isovelocity Surface Area method
190. Pulmonic Valve Cardiac Index (Proximal Isovelocity Surface Area method)
191. Pulmonic Valve Doppler Stroke Index
192. Pulmonic Valve Doppler Stroke Volume
193. Pulmonic Valve Peak Flow, Proximal Isovelocity Surface Area method 194. Pulmonic Valve Stroke Index
195. Pulmonic Valve Stroke Index, Proximal Isovelocity Surface Area method
196. Pulmonic Valve Stroke Volume
197. Pulmonic Valve Stroke Volume, Proximal Isovelocity Surface Area method
198. Pulmonic Vein dimension, diastole/systole
199. Qp (pulmonary flow)
200. Qp (pulmonary flow) Cardiac Index
201. Qp (pulmonary flow) - Qs (systemic flow)
202. Qp (pulmonary flow / Qs (systemic flow)
203. Right Atrium Volume, Area/Length method in diastole
204. Right Atrium Volume, Area/Length method in systole
205. Right Atrium volume, biplane Method of Discs in diastole
206. Right Atrium volume, biplane Method of Discs in systole
207. Right Atrium volume in diastole, View 1
208. Right Atrium volume in diastole, View 2
209. Right Atrium volume in systole, View 1
210. Right Atrium volume in systole, View 2
211. Right ventricular ejection time, corrected
212. Right ventricular preejection period, corrected
213. Right ventricular systolic pressure (from Tricuspid Regurgitation)
214. Right ventricular systolic pressure (from Ventricular Septal Defect)
215. Right Ventricle Cardiac Output (Prolate Ellipsoid method)
216. Right Ventricle Cardiac Output (Pyramidal method)
217. Right Ventricle Cardiac Index (Prolate Ellipsoid method)
218. Right Ventricle Cardiac Index (Pyramidal method)
219. Right Ventricle Ejection Fraction (Pyramidal method)
220. Right Ventricle ejection fraction (Prolate Ellipsoid method)
221. Right Ventricle fractional area change
222. Right Ventricle Stroke Index (Prolate Ellipsoid method)
223. Right Ventricle Stroke Index (Pyramidal method)
224. Right Ventricle Stroke Index, Tricuspid Valve, Proximal Isovelocity Surface Area method
225. Right Ventricle Stroke Volume (Prolate Ellipsoid method)
226. Right Ventricle Stroke Volume (Pyramidal method)
227. Right Ventricle Volume in diastole (Prolate Ellipsoid method)
228. Right Ventricle volume, Pyramidal method in diastole
229. Right Ventricle volume, Pyramidal method in systole
230. Right Ventricle Volume in systole (Prolate Ellipsoid method)
231. Right Ventricle outflow tract Area
232. Right Ventricle Pre-ejection Period / Ejection Time
233. [Site] Area index, Proximal Isovelocity Surface Area method 234. [Site] Area, Proximal Isovelocity Surface Area method
235. [Site] Cardiac Index, Proximal Isovelocity Surface Area method
236. [Site] Cardiac Output, Proximal Isovelocity Surface Area method
237. [Site] Effective Regurgitant Orifice
238. [Site] Peak Flow, Proximal Isovelocity Surface Area method
239. [Site] Pressure gradient
240. [Site] Pressure gradient
241. [Site] Regurgitant Fraction
242. [Site] Regurgitant Volume, Proximal Isovelocity Surface Area method
243. [Site] Stroke Index, Tricuspid Valve Proximal Isovelocity Surface Area method
244. [Site] Stroke Volume, Proximal Isovelocity Surface Area method
245. Superior Vena Cava inspiration/expiration, parasternal long-axis view
246. Superior Vena Cava inspiration/expiration, suprasternal notch short axis view
247. Superior Vena Cava Peak Gradient
248. Superior Vena Cava Peak Velocity, inspiration/expiration
249. Teicholz Volume in diastole
250. Teicholz Volume in systole
251. Tricuspid Regurgitation dp/dt
252. Tricuspid Regurgitation Effective Regurgitant Orifice
253. Tricuspid Regurgitation Regurgitant Fraction
254. Tricuspid Regurgitation Regurgitant Fraction
255. Tricuspid Regurgitation Regurgitant Fraction
256. Tricuspid Regurgitation Regurgitant Volume
257. Tricuspid Regurgitation Volume (2D/2D)
258. Tricuspid Regurgitation Volume by 2D/Doppler
259. Tricuspid Valve A/E(velocity method)
260. Tricuspid Valve annulus area (Biplane Ellipse method)
261. Tricuspid Valve Area, Continuity equation
262. Tricuspid Valve Area index, Continuity equation
263. Tricuspid Valve Area index, Proximal Isovelocity Surface Area method
264. Tricuspid Valve Area, Proximal Isovelocity Surface Area method
265. Tricuspid Valve Cardiac Index, Proximal Isovelocity Surface Area method
266. Tricuspid Valve Cardiac Output, Proximal Isovelocity Surface Area method
267. Tricuspid Valve E/A(velocity method)
268. Tricuspid Valve Peak Flow, Proximal Isovelocity Surface Area method
269. Tricuspid Valve Peak flow rate / Stroke Volume
270. Tricuspid Valve Proximal area
271. Wall Stress (Meridian)
272. Wall Stress (Meridian) (2D, Parasternal short-axis view chordal level)
273. Wall Stress (Meridian) (M-mode)

APPENDIX III

Advanced Development Calc Project

CalcTalk Language Reference Manual

Joe Ruffles
Pete Magsig
Kane Ng

| | |
|---|---|
| Version 1.4 | Acuson Engineering Confidential |
| April 27, 1995 | Copyright © 1994, 1995 Acuson Corp. |

PRELIMINARY

CalcTalk Language Reference Manual

Copyright © 1994, 1995 Acuson Corp.

All rights reserved.

This document contains unpublished technical documentation of Acuson Corporation. This document is intended for use by employees of Acuson Corporation only.

No part of this document may be reproduced outside of the environs of Acuson Corporation, in any form or by any means, without written permission from Acuson Corporation. The copyright notices above do not evidence any actual or intended publication of this document.

Preface

Abstract

The CalcTalk language is designed to describe the calculations and measurements that make up the calc packages. On S Class systems, all calc packages - cardiac, OB, vascular, and any other new packages - will be described in CalcTalk.

Keywords

Sonography, cardiac, OB, vascular, measurement, calculation

Purpose

The purpose of this document is to provide a design reference for developers of the calc talk language and developers of calc talk scripts.

Intended Audience

This document is written for the benefit of people who will write calc talk scripts and the designers of the calc talk language.

How to use this document

Since this document is primarily intended as a reference work, we recommend that you read the introductory sections of the document, and then treat the rest like you would a dictionary: looking up things as you need to. It is recommended that a cursory look-through of all the sections in the document be done prior to attempting to write calc talk scripts.

Syntax Conventions

Examples of calc talk script are presented in the following font:

This is the calc talk example font.

Revision History 0.9     6/19/94         Pete Magsig

Initial creation of the document.

1.0     7/19/94         Joe Ruffles

Developed sections on results, tools, calculations and measurements.. Added complete example. First release to the general populace.

1.1     8/9/94          Pete Magsig

Cleaned up the formatting a little. Created a full book with table of contents. Updated the commands section. Deleted the sections dealing with configs, user settings, and system states.

1.2     3/1/95          Pete Magsig

Fixed numerous errors in the document discovered while prototyping.

1.3     4/13/95         Joe Ruffles

Removed qualifiers and updated example appropriately. Minor touch-ups to several areas..

1.4     4/27/95         Joe Ruffles

Changed the "produces" section of measurements to the "satisfied" predicate.

1.0 The CalcTalk Language

The CalcTalk language is designed to describe the data, calculations, and measurements that make up the calc packages on S class systems. All calc packages - cardiac, OB, vascular, and other potential other packages - will be described in CalcTalk.

A calculation package is described in several ASCII text files containing CalcTalk script. Depending on the organization chosen by its authors, a given calc package might require several hundred files to describe all of its capabilities.

CalcTalk is an interpreted language, but a few simple restrictions allow the system to preresolve some operations to improve runtime performance. The system's design also allows for pre-processed CalcTalk to be stored on production systems for more efficient initialization.

1.1 Why invent a new language?

Previous calc implementations have always been coded in the computer language used by the ultrasound machine. Why take the time and effort to create a whole language for doing calculations and measurements?

- The infrastructure common to all calc packages (e.g., measurement tools, the result database) can be implemented and tested once, and then shared. The details which distinguish one package from another are largely confined to CalcTalk.

- Implementation and specification are done in one place: the CalcTalk language. CalcTalk places emphasis on documenting the clinical behavior of a measurement or calculation as well as providing the implementation for the machine to perform a calc task.

- Developing and refining the Calc packages becomes easier: changes to package content and organization are changes to CalcTalk, not modifications to actual product application ("UISC") code.

- Implementation can be shared by both software developers and Acuson marketing. This can help reduce critical path schedule problems and allow Marketing to pursue new calc options and techniques in a timely manner, without requiring the constant attention of a software developer.

- CalcTalk provides the possibility of special Calc packages for different applications (e.g., pediatric cardiology, high risk OB), custom packages for luminary research, and, eventually, packages customized by end users themselves.

- The same CalcTalk code can be used to guarantee calculation consistency across platforms, e.g., ultrasound machines and the Aegis review station. Engineers from the Aegis Division have already expressed interest in using CalcTalk to implement parts of the Calc system on the Aegis review station..

1.2 The basic terms

*result* - A result is a package of application data in the Calc system (e.g., a head circumference, the point at the peak of a Doppler trace). Results are produced by tools and calculations, and consumed by data fields, reports, worksheet, and other calculations.

*tool* - A tool is something which extracts information from image data (including Aegis images) and produces results which can be used by the Calc system. Examples of tools include calipers, traces, and, potentially, more complex systems such as AM.

*procedure* - A procedure is a series of commands to direct the actions of tools, the ultrasound system, and the Calc system itself. Most procedures are associated with measurements, however there are procedures in CalcTalk that can be associated with power on, calc initialization, and events.

*measurement* - A measurement is a sequence of steps through which the user and the system measure something on the ultrasound image. In CalcTalk, a measurement is a procedure which the user executes by selecting it from a menu.

*calculation* - A calculation is a formula that takes some results as input, processes them, and produces another result as output.

*bulletin board* - The board is the workspace for carrying out measurements. It is a generic container that allows you to "post" and "remove" things from it, e.g. one measurement might post a tool up on the board to be used by another measurement. Or the ultrasound system might post a 'note' to the board saying that a Doppler strip is present on the screen, or that the OB package has been enabled.

1.3 How it all works

When the machine is turned on...

1. The product application looks into the CalcTalk script directory on the hard drive. All files that have the suffix '.ct' are loaded into the product application.

2. If a power up procedure exists in the CalcTalk scripts, it is executed.

3. The Calc system sits and waits for the Calc key.

When the user wants to take a measurement...

1. The user hits the Calc key and the menu comes up.

2. The user selects a measurement from the menu.

3. The scripts are scanned to find the measurements corresponding to the selected measurement. (There can be more than one)

4. The CalcApp looks on the board to see what results, tools, and notes exist. Based on this, it chooses a measurement.

5. The CalcApp executes the commands in the measurement's procedure. These commands will bring up tools, create new results, and other actions, potentially posting these things to the board for other measurements to use.

6. The procedure completes. Things that have been posted to the board are left around. Anything else created in the procedure is destroyed. The exception to this is the results, which, if saved, will remain until explicitly destroyed (either individually, or en masse by the Begin function).

2.0 General CalcTalk structure

A CalcTalk calc specification contains the following.

- Result declarations
- Calculation declarations
- Measurement declarations
- Procedure declarations
- Result collection declarations
- Comments A calc package is described using ASCII Text in standard UNIX files. These files must have the suffix '.ct'. Declarations can appear in any order in any file, i.e. you don't have to declare something before referring to it in the language.

2.1 Names

All names and labels in the language are case sensitive. Names and labels are composed of all upper and lower case letters and numbers and the underscore character ('_'). The following are legitimate names in CalcTalk:

AoV_Vmax
myOwnResult
sumOfTheLengths

Names or labels cannot conflict with any of the key words of the CalcTalk language. These are:

result, measurement, calculation, config, procedure, collection, attach, detach, dim, freeze, strip, generate, new, hide, on, make, post, remove, save, results, show, wait, pause, formula, note, indexnote.

2.2 Comments

Comments are introduced by two slash characters '//' and include all remaining text on the line.

Some examples:

// This is a comment
save results  // This comment follows the save results command.

3.0 Results

Results are the objects which hold the actual data in the Calc system. The user performs a measurement using tools to produce results, and these results are then consumed by calculations to produce other results. Results from both tools and calculations can be displayed in the data field or in reports.

While the result is a basic concept in the Calc system, results can have many properties, and so CalcTalk's result declaration and usage mechanisms have many options. The properties of a result are examined in sections 3.1 through 3.3. Declaring a result is covered in section 3.4, and section 3.5 discusses accessing results.

Note that the properties of a result will often be required to package it into the appropriate DICOM element(s) for Aegis.

3.1 Data Types

Every result has a data type, which is analogous to a data type in a programming language such as C. The data type indicates the form of the result's data and, as a consequence, how it can be used. There is no way to define new data types with CalcTalk itself, although new data types can be added to the language fairly easily as needed.

CalcTalk supports the following data types for results:

1. Value       An undifferentiated number
2. BPoint      B-Mode Point (internal type)
3. BTrace      B-Mode Trace (internal type)
4. BEllipse    B-Mode Ellipse (internal type)
5. Distance    B-Mode or M-Mode linear distance (mm)
6. Depth       B-Mode or M-Mode depth (mm)
7. Duration    A length of time (msec)
8. TimeOfDay   Time stamp (internal type)
9. Date        Calendar date (internal type)
10. BArea      B-Mode Area ($mm^2$)
11. BPerimeter B-Mode Perimeter or Circumference (mm)
12. BLength    B-Mode Trace Length (mm)
13. BAngle     B-Mode Angle (degrees)
14. SDPoint    Spectral Doppler Point (internal type)
15. SDSlope    Spectral Doppler Slope (internal type)
16. SDTrace    Spectral Doppler Trace (internal type)
17. SDVTI      Spectral Doppler Velocity Time Integral (m)

18. Velocity     Doppler Velocity (m/sec)
19. MPoint     M-Mode Point (internal type)
20. MSlope     M-Mode Slope (internal type)
21. HeartRate     Heart Rate (beats per minute)
22. Volume     Volume ($mm^3$)

3.2 Collections

In some applications, it is important to keep multiple instances of a given type of result. In some cases, the requirement is for parallel results to exist for separate entities (e.g., measurements for the individual fetuses in a multiple pregnancy, or measurements for the continuity equation taken before and after provocation with amyl nitrate in a cardiac patient with IHSS). In other cases, the requirement is to be able to take a series of measurements of the same structure so that the results can be averaged or otherwise processed as a group (e.g., a biometry series in OB, or an M-Mode series).

CalcTalk provides the collection mechanism to support these requirements. A collection is declared separately from any particular result, so any result can include references to the collection in its definition.

The collection declaration specifies its name and the indices which are valid for it.

Syntax:

declare collection <name>
{
    <name> [, <name>]
}

This example shows how a could be declared to support multiple fetuses in the OB package:

declare collection fetuses
{
    fetus_a, fetus_b, fetus_c, fetus_d, fetus_e, fetus_f
}

This example shows how a collection could be declared for organizing results based on the stages of an interventionary procedure:

declare collection intervention_stages
{
    pre_intervention, peak_intervention, post_intervention
}

An arbitrary number of collections may be included in the specification of any result. To instantiate a result, indices must be supplied for all collections which are part of its definition.

3.3 Result Declarations

A CalcTalk result declaration specifies the name and type of a result that can be produced, and it specifies any collections that can apply to it. All result declarations must include the result name and type; the collections are optional.

Syntax:

declare result <name>
{
    type {<result type >}
    [ collection {<collection name>} ]
}

All declared results must have unique names; these names are internal to the Calc system and will never be seen by the end user. A separate table will translate from the internal names to those presented to the user.

This example shows how the head circumference result might be declared for OB Calc:

declare result HC
{
    type {BPerimeter}
    collection {multiple_biometry}
    collection {fetuses}
}

When an HC result instance is produced, it will be instantiated with an index for the "multiple_biometry" collection and an index from the "fetuses" collection.

3.4 Accessing Results

The methods of accessing results provide the capability to choose particular result instances based on their collection membership. Only collections which were included in the result's declaration can be specified. Specifications for all collections included in the result declaration must be given (although this can be done implicitly in some cases)

Syntax:

result <local name>
{
    <declared result name>
    {
        <collection name>[<collection index>]
    }
}

Result access statements can be included both in predicates (see section 5.2) and as procedures statements (see the example in section 11.0).

3.5 Accessing Collections of Results

Sometimes there is a need to access a collection of results, usually to perform some operation on the collection (e.g., finding the highest peak velocity in a collection of Velocity results). CalcTalk provides a mechanism for accessing series that is analogous to its method for accessing individual results.

Syntax:

```
collection <local name>
{
    <declared result name> {
        collection-of [<collection name>]
        <collection name> [<collection index>]
    }
}
```

This syntax is very similar to that used for accessing results, except that the collection of interest must also be specified. Note that if the result was declared to use multiple collections, individual indices for those collections must be specified, just as they must be for accessing single results (see section 3.5).

A collection access statement can be used in predicates and in procedures. There are examples of both in the example in section 11.0.

4.0 Measurement Tools

Measurement tools are the interface between real world (e.g., image) data and the Calc system. They are already described in Sequoia specifications, but they appear a bit differently from the perspective of CalcTalk.

4.1 Accessing tools

Tools are specified using their type, i.e. "bm-single-caliper-tool" and an optional name. They are specified in predicates, "make" commands and "get" commands.

Syntax:

```
tool <alias>
{
    <tool type> { <tool name> }
}
```

4.2 Tool Types

CalcTalk provides a set of specialized tools with known behaviors for specific tasks. While some behavior is common to all tools (see the commands in section 7.5.2 "Tool-Specific Commands" on page 26), each tool also has a unique set of commands applicable to its task, and each tool also produces its own particular set of output results, which can be attached to its defined "production sites" (see 7.5.2.4 "result binding" on page 27).

Some tools also take input results.

The complete set of tools which will be available is far richer than is presented in this draft. Consider the following list an example of the types of capabilities supported.

4.2.1 bm-single-caliper-tool

This tool is a single B-Mode caliper.

Specific commands:

1. place-at <BPoint result reference>
   moves the caliper to the location indicated by the BPoint result. This command does not establish a lasting relative placement relationship: if the value of the result changes, the caliper will not automatically move.

2. place-center
   moves the caliper to the center of the displayed image

Production sites:

1. Location (BPoint)
2. Depth (Depth)

4.2.2 bm-pair-caliper-tool

This tool is the standard pair of B-Mode calipers. The LocationTwo and DepthTwo production sites don't return valid results until the second caliper of the pair has been instantiated.

Specific commands:

1. place-at <BPoint result reference>
   moves the current caliper to the location indicated by the BPoint result. This command does not establish a lasting relative placement relationship: if the value of the result changes, the caliper will not automatically move.

2. place-center
   moves the current caliper to the center of the displayed image 3. add-caliper-two
   adds the second caliper, but doesn't display it. commands 4. through 7. are ignored until the caliper two is added.

4. show-caliper-two
   displays caliper two 5. select-caliper-one
   makes caliper one the selected component for attachment 6. select-caliper-two
   makes caliper two the selected component for attachment 7. switch-caliper-selection
   toggles caliper selection between one and two Production sites:

1. LocationOne (BPoint)
2. DepthOne (Depth)
3. LocationTwo (BPoint)
4. DepthTwo (Depth)
5. Distance (Distance)

4.2.3 bm-trace-tool

This tool is the standard B-Mode trace. Its Area production site will not return a valid result until the trace has been completed.

Specific commands:

1. place-start-point-at <BPoint result reference>
   moves the start point (and consequently the entire trace, if it exists) to the location indicated by the BPoint result. This command does not establish a lasting relative placement relationship: if the value of the result changes, the caliper will not automatically move.

2. attach-start-point
   identifies the start point as the component which is to be attached to the trackball when the tool is attached to the trackball.

3. attach-locator
   identifies the locator as the component which is to be attached to the trackball when the tool is attached to the trackball.

4. mark-mode
   puts the tool in mark mode 5. draw-mode
   puts the tool in draw mode Production sites:

1. StartPoint (BPoint)

2. Area (BArea)

3. Perimeter (BLength)

4. TraceData (BTrace)

4.2.4 pw-single-caliper-tool

This tool is a single spectral Doppler caliper.

Specific commands:

1. place-at <SDPoint result reference>
   moves the caliper to the location indicated by the SDPoint result. This command does not establish a lasting relative placement relationship: if the value of the result changes, the caliper will not automatically move.

2. place-vertical <value>
   moves the caliper to the position of the strip indicated by the <value>: 0 or less indicates the bottom of the strip, 1 or greater indicates the top, and a value in between is mapped linearly to a location between the two.

3. lock_horizontal
   prohibits the caliper from horizontal movement relative to the x-axis of the strip.

Production sites:

1. Location (SDPoint)

2. Velocity (Velocity)

3. Time (TimeOfDay)

4.2.5 pw-pair-caliper-tool

This tool is the typical pair of spectral Doppler calipers. Only the "One" production sites product valid results until the second caliper is instantiated. Its specific commands are similar to those for a pair of bB-Mode calipers.

Production sites:
1. LocationOne (SDPoint)
2. VelocityOne (Velocity)
3. TimeOne (TimeOfDay)
4. LocationTwo (SDPoint)
5. VelocityTwo (Velocity)
6. TimeTwo (TimeOfDay)
7. Slope (SDSlope)
8. DeltaVelocity (Velocity)
9. DeltaTime (Duration)

4.2.6 mm-single-caliper-tool

This tool is a single sm-mode caliper.

Specific commands:
1. place-at <MPoint result reference>
   moves the caliper to the location indicated by the MPoint result. This command does not establish a lasting relative placement relationship: if the value of the result changes, the caliper will not automatically move.
2. place-vertical <value>
   moves the caliper to the position of the strip indicated by the <value>: 0 or less indicates the bottom of the strip, 1 or greater indicates the top, and a value in between is mapped linearly to a location between the two.
3. lock_horizontal
   prohibits the caliper from horizontal movement relative to the x-axis of the strip.

Production sites:
1. Location (MPoint)
2. Depth (Depth)
3. Time (TimeOfDay)

4.2.7 mm-delta-caliper-tool

This tool is a single m-mode caliper that operates off of an anchor point which is set with a specific tool command. It can report values based on the location of its caliper relative to the anchor point.

Specific commands:

1. anchor-at <MPoint result reference>
   sets the anchor point.

2. place-at <MPoint result reference>
   moves the caliper to the location indicated by the MPoint result. This command does not establish a lasting relative placement relationship: if the value of the result changes, the caliper will not automatically move.

3. place-vertical <value>
   moves the caliper to the position of the strip indicated by the <value>: 0 or less indicates the bottom of the strip, 1 or greater indicates the top, and a value in between is mapped linearly to a location between the two.

4. lock_horizontal
   prohibits the caliper from horizontal movement relative to the x-axis of the strip.

Production sites:

1. Location (MPoint)

2. Depth (Depth)

3. Time (TimeOfDay)

4. Distance (Distance)
   This result is the distance from the anchor to the caliper. This result will be automatically updated by either caliper movement or a change in the value of the consumed MPoint result.

5. DeltaTime (Duration)
   This result is the difference in time (the strip x axis) between the anchor and the caliper. This result will be automatically updated by either caliper movement or a change in the value of the consumed MPoint result.

6. Slope (MSlope)
   This result is the slope of the line from the anchor to the caliper. This result will be automatically updated by either caliper movement or a change in the value of the consumed MPoint result.

5.0 Measurements

A measurement is made when the user brings up a tool or tools and measures something on the ultrasound image. A measurement has a name that corresponds to an entry in the measure menu structure. When a measurement is selected from the measure menu structure, all measurements are scanned to find a corresponding match between the name of the measurement selected and the preconditions for that measurement.

5.1 Basic Measurement Structure

Syntax:

```
declare measurement <name>
{
    enable {
        <predicate expression>
    }
    select {
        <predicate expression>
    }
    collection { <collection name> }
    satisfied {
        < predicate expression >
    }
    procedure
    {
        requires{ <predicate expression> }
        commands { <commands> }
    }
}
```

A measurement is composed of six sections, some of which are optional:

1. The 'enable' section. This section contains a set of conditions that allow this measurement to be enabled in the ultrasound system. If these conditions are not met, then the ultrasound user doesn't even know that the measurement exists. This section is optional; if omitted, it defaults to "always true". See 5.2 "Predicates" for details.

2. The 'select' section. This section contains a set of conditions that tell whether or not the measurement should appear in the measure menu. This section is optional; if omitted, it defaults to "always true". See 5.2 "Predicates" for details.

3. The 'collection' section. This section specifies that all input and output results which are declared to use a particular collection will use the same index of that collection unless specifically overridden.

4. The 'satisfied' section. This section specifies the results which will be produced by the measurement. The 'satisfied' section allows the system to know whether or not the products of a measurement already exist (and so how to appropriately highlight the measurement's name in the menu).

5. The 'procedure' section. This section is where the actual work gets done. It contains the series of actions that make up the measurement. See 7.0 "Procedures" for details on procedures. The procedure section can either be of the form "procedure { procedure body }" or "procedure <procedure name>". Calls to another procedure can also be included within a procedure.

An example measurement is given in section 5.3.

5.2 Predicates

A predicate is an expression that evaluates to a true or false condition. Predicates appear in the enable, select, and requires section of measurements and in 'if' commands. A predicate tries to match the objects listed in it with objects that have been posted to the board. If these objects match according to the expression, then the predicate evaluates to true, otherwise it evaluates to false.

Predicates support grouping by ()'s and the following operators. Operators are in bold face.

$a$ AND $b$      If a and b both exist, then this is true.

$a$ OR $b$      If either a or b exist, then this is true.

NOT $b$      If a is true, then this is false. If a is false, then this is true.

$a$ and $b$ here correspond to expressions or objects. An object by itself evaluates to true if the object exists.

5.2.1 Predicate objects

The objects that can appear in a predicate are results, tools, configs, system-states, and user-settings. The following is the syntax of a predicate object:

<type> <name> { <specification> }

<type> can be either result, tool, or note.

<name> is the name that the object will be referred to in commands executed by a procedure following this predicate. The name is optional.

<specification> is information that uniquely identifies this object on the board. This varies with the type of the object. The specification is surround by curly braces.

Result and collection access statements (discussed in sections 3.5 and 3.6, respectively) are examples of predicate objects.

Other examples:

```
note { B-mode-image }
note { Vmax-from-DopplerTrace { off } }
index index_value { MM-Series-Confederation }
```

5.3 An Example of a Typical Measurement

This example shows what a basic measurement of a spectral Doppler velocity might look like in CalcTalk.

```
//===========================================================
//
// This is a prototype of what an AoV-Vmax
// measurement might look like.
//
declare measurement AoV-Vmax
{
    enable { note { cardiac-purchased } }
    select { note { Vmax-from-DopplerTrace { off } } }
    satisfied { result { AoV-Vmax } }
    procedure
    {
        requires { note { B-mode-image } AND
                   note { PW-doppler-strip } }
        commands
        {
            make tool caliper { pw-single-caliper-tool }
            make result vmax { AoV-Vmax }
            post caliper
            change caliper
            {
                place_vertical 0.50
                vmax->Velocity
                attach
                show
            }
            wait for enter
            change caliper
            {
                detach
            }
        }
    }
}
```

6.0 Calculations

Calculations take in some number of results as input, perform some processing of those results, and produce another result as output. CalcTalk provides a rich set of operators for performing that processing, and it also provides a number of facilities for enabling and choosing which calculation to perform.

6.1 Basic Calculation Structure

The basic structure of a calculation is similar to that of a measurement. There are the same predicates for availability and matching inputs, there is a produces section to identify the produced result, and there is the capability to vectorize the calculation across collections. The main difference is that instead of a procedure with commands, there is a formula section which contains an expression for producing the output.

In addition, the local names used inside of a calculation cannot have hyphens in them, to prevent potential ambiguity with the use of the minus sign.

Syntax:

```
declare calculation <name>
    enable
    {
        <predicate expression>
    }
    select
    {
        <predicate expression>
    }
    requires
    {
        <predicate expression>
    }
    collection { <collection name> }
    produces
    {
        <result specification>
    }
    formula
    {
        <mathematical formula>
    }
```

A measurement is composed of six sections, some of which are optional:

1. The 'enable' section. This section contains a set of conditions that allow this calculation to be enabled in the ultrasound system. If these conditions are not met, then the ultrasound user doesn't even know that the measurement exists. This section is optional; if omitted, it defaults to "always true". See 5.2 "Predicates" for more details.

2. The 'select' section. This section contains a set of conditions that tell whether or not the use has selected this calculation. This section is optional; if omitted, it defaults to "always true".

3. The 'requires' section. These are the preconditions for instantiating this calculation. The calculation will only be instantiated if the things specified in the requires block exist. The requires section is technically optional. If it isn't specified, then there are no preconditions for calculation and it will always be instantiated. In practice, this would not be very useful behavior, since most useful calculation require results as input.

4. The 'collection' section. This section specifies that all input and output results which are declared to use a particular collection will use the same index of that collection unless specifically overridden.

5. The 'produces' section. This section specifies the result which will be produced by the calculation. A calculation must produce exactly one result - not multiple results, and not a series.

6. The 'formula' section. This section is where the actual work gets done. It contains the formula for computing the produced result.

6.2 Calculation Formulas

All calculation formulas are of the following form:

<output result object> = <expression> where <expression> is one of (<unary operator> ( <single result value> ))
(<collection operator> ( <collection value> ))
(<single result value> <infix binary operator> <single result value>)

Other types of expressions could be added as necessary to support future growth. Each of the current supported types of expressions is described in turn in the following sections. The distinction between "result objects" and "result values" (and similarly between "collection objects" and "collection values") indicates that results aren't actually created to perform the intermediate in a calculation's formula. This detail is only important for those concerned with the implementation of calculations; the author CalcTalk scripts should consider the term equivalent.

Note that all expressions MUST be enclosed in parentheses. This is to make the order of operations completely unambiguous to the both the author of CalcTalk scripts and anyone who might have occasion to parse a formula visually.

6.2.1 Unary Operators

The unary operators take one result value as input, and produce another result as output. The supported unary operators are given in Table 1. "CalcTalk Unary Operators" on page 19. The list of available operators is expected to grow as needed to support calc formulas, and the given operators should be considered examples of the type of processing available.

Note that most of the mathematical operations are done on results of type 'Value', which carry no special information about units. The VALUE operator, which performs a conversion from some scalar type with units to a unitless 'value', will be supplied implicitly to convert typed results to 'values' for these operators.

| Operator | Input Type | Output Type | Processing |
|---|---|---|---|
| ABS | Value | Value | Absolute Value |
| ACOS | Value | Value | Arcosine |
| ASIN | Value | Value | Arcsin |
| ATAN | Value | Value | Arctangent |
| COS | BAngle | Value | Cosine |
| COS | Value | Value | Cosine |
| DEPTH | MPoint | Depth | Returns depth of at given point. |
| LN | Value | Value | Natural Log |
| LOG | Value | Value | Log base 10 |
| RECIP | Value | Value | Reciprocal |
| SAMPLETIME | MPoint | TimeOfDay | Returns time stamp at given point. |
| SAMPLETIME | SDPoint | TimeOfDay | Returns time stamp at given point. |
| SIN | BAngle | Value | Sine |
| SIN | Value | Value | Sine |
| SQR | Value | Value | Square |
| SQRT | Value | Value | Square Root |
| TAN | BAngle | Value | Tangent |
| TAN | Value | Value | Tangent |
| SAMPLETIME | MPoint | TimeOfDay | Returns time stamp at given point. |
| SAMPLETIME | SDPoint | TimeOfDay | Returns time stamp at given point. |

Table 1. CalcTalk Unary Operators

| Operator | Input Type | Output Type | Processing |
|---|---|---|---|
| VALUE | Any non-internal type | Value | Strips special units and converts to a 'Value'. |
| VELOCITY | SDPoint | Velocity | Returns velocity at given point. |

Table 1. CalcTalk Unary Operators

6.2.2 Collection Operators

The collection operators take a collection as input, and produce either a value, a new result of the collection's type, or a reference to one of the results in the collection. Here the distinction between a new result and a reference is important - a new result is derived from the collection members while a reference *is* one of the collection members.

The supported collection operators are given in Table 1. "CalcTalk Unary Operators" on page 19. The list of available operators is expected to grow as needed to support calc formulas, and the given operators should be considered examples of the type of processing available.

| Operator | Input Type | Output Type | Processing |
|---|---|---|---|
| FREEINDEX | Any Collection | Index value from collection | Returns an available index, or NULLINDEX if none available. |
| MAX | Any Collection of Scalar Results | Result from collection | Result with most positive value. |
| MEAN | Any Collection of Scalar Results | Result of collection type | Average of collection values. |
| MEMBERS | Any Collection | Value | Number of elements in collection. |
| MIN | Any Collection of Scalar Results | Result from collection | Result with most negative value. |
| NEWEST | Any Collection | Result from collection | Most recently instantiated result. |
| OLDEST | Any Collection | Result from collection | Least recently instantiated result. |

Table 2. CalcTalk Collection Operators

6.2.3 Binary infix operators

The binary infix operators take two inputs and produce an output. They are written in the traditional algebraic form, with the operator between its two operands (hence the name "infix").

A list of supported operators is given in Table 1. "CalcTalk Unary Operators" on page 19. Like the other tables of operators, this one should be taken as an example of the types of processing available. New operators can be added as needed to support calculations.

| Operator | Left Operand Input Type | Right Operand Input Type | Output Type | Processing |
|---|---|---|---|---|
| + | Any scalar result | Any scalar result of matching type | Scalar result of matching type | Sum of the operands |
| - | Any scalar result | Any scalar result of matching type | Scalar result of matching type | Left operand minus the right operand |
| / | Value | Value | Value | Left operand divided by the right operand |
| * | Value | Value | Value | Product of the operands |
| ** | Value | Value | Value | Left operand raised to the power indicated by the right operand |
| DIST | BPoint | BPoint | Distance | Distance between the two points. |
| DIST | MPoint | MPoint on same M-Mode line. | Distance | Distance between the two points. |

Table 3. CalcTalk Binary Infix Operators

7.0 Procedures

Procedures are series of commands. Procedures are usually associated with measurements, but they can also stand alone by themselves. Certain procedures have reserved names and get executed when the system starts up.

Syntax:

```
declare procedure <name>
{
    requires { <predicate expression> }
    commands
    {
        <commands>
    }
}
```

When used in a measurement, the declare keyword and <name> are left out. Procedures have two basic parts:

1. The 'requires' section contains a predicate. If this predicate does not evaluate to true, then the procedure will not be executed. This section is optional. If it is not there, then the procedure will always be executed.

2. The 'commands' section contains the commands that the procedure will execute, in order, if the predicate is true.

7.1 Flow of control

There are two ways to change the flow of control in a procedure: "if" statements and "on" statements.

7.1.1 If statements

An if statement has the following syntax:

```
if { <predicate expression> } commands
{
    <commands>
}
else commands
{
    <commands>
}
```

If the predicate is true, then the commands after the if is executed, otherwise the commands after the else is executed.

7.1.2 On statements

An on statement has the following syntax:

on <event> do commands { <commands> } or, alternately, on <event> do procedure <name> or, alternately, on <event> do measurement <name>

The on statement sets up an interrupt that will last until the end of the procedure in which it is declared. If the specified event occurs at any time within this procedure, then the commands, procedure, or measurement after the on statement will be executed. All of the existing tools, results, etc. that are being worked on in this procedure will be transferred to the new procedure or measurement. They can be referred to by the names they were given in this procedure.

It is important to be careful using the on statement, since the availability of names in the target procedure/measurement is not guaranteed.

7.2 Scope

Commands refer to objects by the names given to them in the predicates, 'make', and 'get' commands. An object must exist for a command to operate on it. The name given to the object will be local to the procedure and to any embedded 'if' procedures.

7.2.1 NOT operator side effects

If a NOT operator is used in a predicate, this necessitates that any object embedded in the NOT operator cannot be referenced in the procedure, since it does not exist. Of course, if the NOT operator is embedded within another NOT operator, this side effect is not true.

7.3 Events

At any time in a procedure, an event may come in from the system. This event is usually the result of user input. Events can be caught through the use of the 'on' command.

The following events are currently defined. The set of events should be expected to grow as the system is developed.

7.3.1 abort

An abort event occurs whenever the user does something that signals to calc that the user doesn't want to do calculations any more. This events default behavior is to jump to the end of the procedure and do the end of procedure cleanup routine.

7.3.2 enter

An enter event occurs when the user officially enters a result. This can come from the enter softkey or any other condition from the keyboard that signals 'enter'.

7.3.3 trace-tool-key

A trace-tool-key event means that the user has hit the trace tool key.

7.3.4 ellipse-tool-key

An ellipse-tool-key event means that the user has hit the ellipse tool key.

7.3.5 caliper-tool-key

A caliper-tool-key event means that the user has hit the caliper tool key.

7.4 When the procedure ends

When the procedure ends, all tools and results that were created in this procedure are destroyed and all 'on event' interrupts are wiped clean. To prevent results from being destroyed you have to execute the 'save results' command. This will save all results that have been created in the procedure. To keep tools from being destroyed, post them to the board.

7.5 Commands

7.5.1 CalcTalk Commands

7.5.1.1 change

Directs a series of commands to a particular object, usually a tool. The tool specific commands are discussed in 7.5.2.

```
change <object name>
{
    <object specific commands>
}
```

7.5.1.2 generate new calculations

Generates any new calculations that might be created from the existing results.

Syntax:

```
generate new calculations
```

7.5.1.3 freeze strip

Freezes the strip.

Syntax:

```
freeze strip
```

7.5.1.4 freeze two-D

Freezes the 2D image(s) (B-Mode and/or Color Doppler).

Syntax:

freeze two-D

7.5.1.5 make

Makes the given object. An object created with make will be destroyed at the end of the procedure unless posted. An exception here is results, which use require the 'save results' command to prevent from being destroyed.

Syntax:

make <object type> <name> { <object specification.> }

<object type> is one of: result, tool, calculation.

<name> is the name that this object will have inside the procedure so other commands can refer to it.

<object specification> is the name of the object given in the object declaration and any specification necessary to create that object.

7.5.1.6 pause

Pauses for the specified number of milliseconds.

Syntax:

pause <milliseconds>

<milliseconds> is the number of milliseconds to pause before doing something.

7.5.1.7 post

Posts an object to the board.

Syntax:

post <object name>

<object name> is the name of the object to post to the board. This must be the name of the object that was specified in the make command.

7.5.1.8 remove

Removes an object from the board.

Syntax:

remove <object type> { <object specification> } or, alternately, remove <object name>

<object type> is one of: result, tool, calculation.

<object specification> is the name of the object given in the object declaration and any specification necessary to locate that object on the board.

<object name> is the name an object was given in a predicate or make statement.

Note that removing some objects, such as results which are already in use in calcularions, can have cascading consequences. This may be desired behavior, of course.

7.5.1.9  save new results

Commits any newly created results.

Syntax:

save new results

7.5.1.10  set collection index

Sets the index of a collection which was identified in the measurement's collection section (described in section 5.1). This command must be included exactly once for each collection that was specified in the collection section, and it must be executed before any results are produced which require implicit specification of its collection.

Syntax:

<collection name>(<collection index>)

where <collection index> is the name of an index or typically an object of type 'indexnote'. This construct is used in the example given in section 11.0.

7.5.1.11  wait for

Waits for a specific event to occur. All CalcTalk execution is halted until this event occurs.

Syntax:

wait for <event>

<event> is as described in 7.3.

7.5.2  Tool-Specific Commands

The tool specific commands are issued from within a change block, discussed in section 7.5.1.1. While the exact commands will vary from tool to tool, all tools respond to the following commands:

7.5.2.1  attach

Attaches the tool to the trackball. The tool will become Calc's currently attached tool, detaching any previously attached tool. Actual trackball attachment requires that Calc be allocated the trackball from the function stack handler, and that Calc be in a state to attach tools to the trackball (in other words, this tool will be attached to the trackball, but only when Calc owns the trackball and only when Calc is not using the trackball for something else, like the pop-up menu).

Syntax:

attach

7.5.2.2 detach

Detaches the tool from the trackball. Executing this command leave no tool attached to the trackball. It does NOT automatically attach another tool, and it does not cause Calc to drop its request for the trackball from the function stack handler.

Syntax:

detach

7.5.2.3 hide

Makes the tool invisible (the opposite of show, in section 7.5.2.5). Hiding a tool does not automatically detach it, or cause it to stop producing results.

Syntax:

hide

7.5.2.4 result binding

This command uses an operator to bind a particular result instance to a production site on a tool. Each tool will have a different set of production sites, corresponding to the types of results that it can produce.

Syntax:

<result name>-><binding site name> where <object name> refers to a result instance from a 'make' command.

7.5.2.5 show

Shows a tool.

Syntax:

show

8.0 Notes

Notes are items which can be posted to the board to pass information among procedures. There are currently two types of notes defined.

8.1 Standard Notes

Standard notes, or "notes", are just strings posted to the board. Once posted, their existence can be tested in predicated.

The syntax a make command for a note is:

make note <local name> { <name> { <value> } }

And the predicate test for a standard note is:

note <local name> { <name> { <value> } }

One reason to get an object name for a note is so that it can be removed with the "remove" command (see section 7.5.1.8).

9.0 Indexes

Indexes contain a collection index. An index object can be used in any situation that calls for a collection index, provided of course that the index was created with an index from the appropriate collection.

Index are created using the make command (see section 7.5.1.5) with the following syntax:

> make index <local name> { <collection index> { <index name> } } where <local name> give a local name for the note, which can be used to post it, and <index name> gives a name by which the note can be found on the board by another procedure.

The access statement and predicate test for an indexnote refers to it by its name:

> index <local name> {<index name>}

Indexnotes are used in the example given in section 11.0.

Appendix A  A complete example

This example illustrates how the series of M-Mode measurements described in the Cardiac Calc functional specification could be coded using CalcTalk. This series of measurements is one of the most complex to perform (for a less intimidating example, see section 5.3), because it requires a group of independent measurements to be coordinated in a "confederation":

1. The measurement tools for each confederation must be locked on one M-Mode line.

2. Each independent measurement can involve tools which are shared with up to two other measurements.

3. The user must be able to turn off (and thus remove from the series) any combination of measurements.

4. The user must be able to start the series with any measurement (although the series cannot continue past the selection of LVPW, its last measurement).

5. Calculations must be performed both within and across confederations.

All of the measurement results are declared, as are two representative calculations (fractional shortening, within a confederation, and mean IVS, across confederations), their corresponding calculated results, and the measurements necessary to produce the IVS measurement results. The other measurements in the series would be very similar in form.

```
// We need two sets of results, one for systole and one for
// diastole, so we can use a collection to distinguish between them.
// To make a result which has been declared with the card_cycle
// collection, we must specify the member of the collection to which
// it corresponds (i.e., is it the result for systole or diastole?).
declare collection card_cycle {systole, diastole}

// Declare a collection to let us average 5 sets of measurements.
// There can be up to one (1) systolic and diastolic confederation
// for each index.

declare collection m_mode_series { 1, 2, 3, 4, 5 }
```

```
// The following five results are the distance results that are the
// objective of the M-Mode series of measurements. They are seen in the
// report, as are their mean values. For the purpose of illustration, we
// will also use them to calculate fractional shortening.

// This is the distance between RVWStart and RVWEnd
declare result RVW
{
    type { Distance }
    collection{m_mode_series}
    collection{card_cycle}
}

// This is the distance between RVWEnd and IVSStart
declare result RVD
{
    type{Distance}
    collection{m_mode_series}
    collection{card_cycle}
}

// This is the distance between IVSStart and IVSEnd
declare result IVS
{
    type{Distance}
    collection{m_mode_series}
    collection{card_cycle}
}

// This is the distance between IVSEnd and LVPWStart
declare result LVD
{
    type{Distance}
    collection{m_mode_series}
    collection{card_cycle}
}

// This is the distance between LVPWStart and LVPWEnd
declare result LVPW
{
    type{Distance}
    collection{m_mode_series}
    collection{card_cycle}
}
```

```
// The following six results are points on the M-Mode strip. They
// are communicate information among the tools which take the
// confederated measurements.

// Point at the start of the RVW
declare result RVWStart
{
    type{MPoint}
    collection{m_mode_series}
    collection{card_cycle}
}

// Point at the end of the RVW
declare result RVWEnd
{
    type{Mpoint}
    collection{m_mode_series}
    collection{card_cycle}
}

// Point at the start of the IVS
declare result IVSStart
{
    type{MPoint}
    collection{m_mode_series}
    collection{card_cycle}
}

// Point at the end of the IVS
declare result IVSEnd
{
    type{MPoint}
    collection{m_mode_series}
    collection{card_cycle}
}

// Point at the start of the LVPW
declare result LVPWStart
{
    type{MPoint}
    collection{m_mode_series}
    collection{card_cycle}
}

// Point at the end of the LVPW
declare result LVPWMMEnd
```

```
        // Or the series doesn't even exist yet.
        (NOT collection { MMSeriesLocks
                        collection-of[m_mode_series]
                        card_cycle[diastole] } ))
} commands {

// Start the confederation
    procedure start_new_mm_diastole_series

// Get the confederation index that was posted.
    get index confedidx { MM-D-Series-Confed }

// Set the implicit collection index.
    m_mode_series[confedidx]

// Get the horizontal lock that was created. Because this is the
    // start of the confederation, we will supply its value.
    get result lock { MMSeriesLock card_cycle[diastole] }

// Make the necessary results
    make result width { IVS { card_cycle[diastole] } }
    make result start { IVSStart { card_cycle[diastole] } }
    make result end { IVSEnd { card_cycle[diastole] } }

// Make the first caliper.
    make tool initial_caliper { mm-single-caliper-tool }
    post initial_caliper // Send this block of commands to the tool, in this order.
    change initial_caliper
    {
        // Place is half way down the strip.
        place_vertical 0.50

// Location result will be horizontal lock
        lock->Location

// Location result is also IVSStart
        start->Location

// Connect it to the trackball
        attach
```

```
        // Finally, let the user see it.
        show
}

// Wait for the user to enter the caliper value.
wait for enter

// We're now locked onto a horizontal line.
change initial_caliper
{
    detach
    lock-horizontal
}

// Now make the second caliper for the IVSEnd.
make tool delta_caliper { mm-delta-caliper-tool }
post delta_caliper change delta_caliper
{
        // Base the delta value off of the start value.
        anchor-at start // Place the locator at the IVSStart.
        place-at start // Now that its placed, lock its horizontal movement.
        lock-horizontal // The produced location is the IVSEnd.
        end->Location // The produced distance is the IVS.
        width->Distance // Connect it to the trackball.
        attach // Let the user see it.
        show
}

// Wait for the user to enter the caliper value.
wait for enter

// We're now locked onto a horizontal line.
```

```
        change initial_caliper { detach } save new results pause 500

}
}
```

```
// This declaration of the IVSd measurement handles the typical case
// in which the IVSStart point already exists from the previous
// measurement of RVD.
declare measurement IVSd { enable { note { cardiac-purchased } } select { note { MM-IVSd-Selected { on } } }

// This vectorizes the measurement across the m_mode_series
    // collection. This index will in turn be used to make the output
    // results.
    collection { m_mode_series } satisfied
    {
        result  { IVS  { card_cycle[diastole] } }
        result   { IVSEnd { card_cycle[diastole] } }
    } procedure
    {
        // This version of the measurement is the one that begins the
        // confederation.
        requires
        {
            // Must have M-Mode.
            note { M-mode-image } AND // Confederation must be in progress.
            index confedidx { MM-D-Series-Confed } AND // IVSStart was obtained from measuring RVD
            result start { IVSStart card_cycle[diastole] }
        } commands {
            // Set the implicit collection index.
            m_mode_series(confedidx) ??????? Pete?

// make the required results
            make result width { IVS  { card_cycle[diastole] } }
            make result end { IVSEnd { card_cycle[diastole] } }

// Get the horizontal lock that was created. We will only use its
            // value. Note the use of the implicit collection index.
```

```
        get result lock { MMSeriesLock card_cycle[diastole] }

// Now make the caliper for the IVSEnd.
    make tool delta_caliper { mm-delta-caliper-tool }
    post delta_caliper change delta_caliper
    {
        // Base the delta value off of the start value.
        anchor-at start // Place the locator at the IVSStart.
        place-at start // Now that its placed, lock its horizontal movement.
        lock-horizontal // The produced location is the IVSEnd.
        end->Location // The produced distance is the IVS.
        width->Distance // Connect it to the trackball.
        attach // Let the user see it.
        show
    }

// Wait for the user to enter the caliper value.
    wait for enter

// We're now locked onto a horizontal line.
    change initial_caliper { detach } save new results pause 500
    }
  }
}
```

```
// This declaration of the IVSd measurement handles the less typical case
// in which the confederation exists, but the IVSStart point doesn't
// (because, say, the RVD measurement is turned off).
declare measurement IVSd { enable { note { cardiac-purchased } } select { note { MM-IVSd-Selected { on } } }

// This vectorizes the measurement across the m_mode_series
    // collection. This index will in turn be used to make the output
    // results.
    collection { m_mode_series } satisfied
    {
        result  { IVS card_cycle(diastole)}
        result  { IVSStart card_cycle(diastole)}
        result  { IVSEnd card_cycle(diastole)}
    } procedure
    {
        // This version of the measurement is the one that begins the
        // confederation.
        requires
        {
            note { M-mode-image } AND // Confederation must already exist.
            index confedidx { MM-D-Series-Confed }) AND // there is no IVSStart yet.
            NOT result { IVSStart { card_cycle[diastole] } }
        } commands {

// Set the implicit collection index.
            m_mode_series(confedidx) // ???????

make result width { IVS card_cycle(diastole)}
            make result start { IVSStart card_cycle(diastole)}
            make result end { IVSEnd card_cycle(diastole)}

// Get the horizontal lock that was created. We will only use its
```

```
// value.
get result lock { MMSeriesLock { card_cycle[diastole] } }

// Make the first caliper.
make tool initial_caliper { mm-single-caliper-tool }
post initial_caliper change initial_caliper
{
    // Horizontal location is based on confederation lock.
    place-at lock
    lock-horizontal // Vertical position is half way down the strip.
    place-vertical 0.50

// Location result is IVSStart
    start->Location

// Connect it to the trackball
    attach

// Finally, let the user see it.
    show
}

// Wait for the user to enter the caliper value.
wait for enter change initial_caliper { detach }

// Now make the caliper for the IVSEnd.
make tool delta_caliper { mm-delta-caliper-tool }
post delta_caliper change delta_caliper
{
    // Base the delta value off of the start value.
    anchor-at start // Place the locator below the IVSStart.
    place-below start
    lock-horizontal // The produced location is the IVSEnd.
    end->Location
```

```
    // The produced distance is the IVS.
    width->Distance

// Connect it to the trackball.
    attach

// Let the user see it.
    show
  }

// Wait for the user to enter the caliper value.
  wait for enter

// We're now locked onto a horizontal line.
  change initial_caliper { detach } save new results pause 500
    }
  }
}
```

```
// This is the demographic header panel
declare panel card_demo_header
{
    // This panel is enabled if cardiac calc in enabled.
    enable { note { cardiac-purchased } } initialization {
        // Specifies the required input data.
        requires {
            note { CardiacCalcActive }
            result name { PtName }
            result date { Date }
            result id   { PtId }
        }
        commands {
            make panel { DemoPanel }
            post panel { MyPaneL } change panel
            {
                name-> PatientName
                date-> ExamDate
                id-> PatientId
            }
        }
    } update {
        requires { panel { MyPanel } }

// These will be used if they are available.
        uses {
            result bsa { BSA }
            result exam_type { ExamType }
        }
        commands {
            change panel
            {
                if { bsa } commands { bsa->BodySurfaceArea }
                if { exam_type } commands { exam_type->ExamType }
            }
        }
    }
}
```

```
// These are the measurements for taking the IVS measurement
// for diastole.

// This first measurement declaration is for the version which is
// available if there is not a current confederation underway, but
// there is room to add a new confederation.
declare measurement IVSd {

// Only available if cardiac calc is paid for.
    enable { note { cardiac-purchased } }

// The user could have chosen to turn this measurement off,
    // in which case this predicate would fail and the measurement
    // would never be seen in the menu.
    select { note { MM-IVSd-Selected { on } } }

// This vectorizes the measurement across the m_mode_series
    // collection. This index will in turn be used to make the
    // output results.
    collection { m_mode_series }

// Remember, we have made the m_mode_series index implicit in all
    // of these produced results.
    satisfied
    {
        result  { IVS { card_cycle[diastole] } }
        result  { IVSStart { card_cycle[diastole] } }
        result  { IVSEnd { card_cycle[diastole] } }
    } procedure
    {
        requires
    {

// Must be in M-Mode
        note { M-mode-image } AND

// Can't have a confederation in progress
        NOT index confedidx { MM-D-Series-Confed } AND // Must have room for a new confederation. Either the series
        // exists, but has room for another...
        ( ( collection locks {MMSeriesLocks
                        collection-of[m_mode_series]
                        card_cycle[diastole] } AND
            FREEINDEX(locks) ) OR
```

```
{
    type{MPoint}
    collection{m_mode_series}
    collection{card_cycle}
}

// This collection of results is only used internally. It holds the
// x-axes necessary to lock each confederation of tools on one M-Mode
// line.
declare result MMSeriesLock
{
    type{MPoint}
    collection{m_mode_series}
    collection{card_cycle}
}
```

```
// Calculated LV Fractional shortening. This result doesn't have a
// card_cycle collection, because it is calculated across systole and
// diastole for one element of the series.
declare result LV_FS
{
    type{Value}
    collection{m_mode_series}
}

// Calculated mean IVS. Note that unlike the other results, this one
// was not declared with the m_mode_series collection. That's because
// there's only one of this result per series.
declare result AvgIVS
{
    type{Value}
    collection{card_cycle}
}
```

```
// This is the calculation of the LV Fractional shortening
declare calculation CalcLVFractShort
{
    // Could be anything; intended for encryption. Defaults to always
    // enabled if omitted.
    enable { note {cardiac_purchased} }

// Could be anything; intended for user set-up. Defaults to always
    // selected if omitted.
    select {note { Fractional-Shortening-From-MMode { on } }

// This vectorizes the equation across the m_mode_series collection.
    // The m_mode_series indices for the input results must match, and
    // this index will in turn be used to make the output result.
    collection {m_mode_series}

// Specifies the required inputs and binds them to local names which
    // are used in the formula.
    requires
    {
        result d { LVD { card_cycle[diastole] } } AND
        result s { LVD { card_cycle[systole] } }
    }

// Identifies the resulting output and gives it a local name for
    // use in the formula. Note that the produced result will have no
    // card_cycle collection, but will get an m_mode_series collection
    // index automatically because of the collection declaration above.
    produces
    {
        result p { LV_FS }
    }

// This is the actual calculation. Note that parentheses are required
    // because there is (deliberately) no built-in operator precedence.
    formula
    {
        // (Wide - Narrow) / Wide
        p = ((d - s) / d)
    }
}
```

```
// This is the calculation of the Average Intervetricular Septum
declare calculation CalcAvgIVS
{
    // This calculation is always enabled and selected. All it needs are
    // its required input results.

// Specifies the required input, which is a series, and binds it to a
    // local name which is used in the formula. Note that we have to
    // specify which card_cycle collectioncollection we want.
    requires
    {
        collection ivs_series { IVS {
                            collection-of[m_mode_series]
                            card_cycle[diastole] }
    }

// Identifies the resulting output and gives it a local name for use
    // in the formula. Note that we must specify the card_cycle collection
    // because you can't create an AvgIVS without one.
    produces
    {
        result avg { AvgIVS { card_cycle[diastole] } }
    }

// This is where the actual work gets done.
    formula
    {
        // Built in operators do all the work because MEAN() knows how to
        // average results of type Distance.
        avg = MEAN(ivs_series)
    }
}
```

```
// This procedure is used to start a "confederation" of M-Mode calipers
// for the series. It assumes that the collection of interest has a free
// index available; that condition should be tested in the predicate of
// the main measurement procedure.
declare procedure start_new_mm_diastole_series
{ commands {
        // Get the current collection of lock points so that we can find a
        // free index for the new lock point we're about to create.
        get collection locks { MMSeriesLocks { card_cycle[diastole] } }

// Make the indexnote which identifies the confederation under
        // construction and put it on the board.
        make index confedidx { MM-D-Series-Confed  FREEINDEX(locks)}
        post confedidx // Now, make the result which will identify this series' M-Mode line.
        // If we wanted to get fancy and specify an initial (unlocked) x
        // location based on existing results (say, a beat to the right of the
        // last one that we measured) we could do that here, and then re-write
        // the measurements to take that initial value before then lock the
        // x axis.
        make result new_lock { MMSeriesLock {
                    card_cycle[diastole]
                    m_mode_series[confedidx] } }
    }
}
```

It is claimed:

1. An ultrasound measurement system for performing a plurality of ultrasound measurements, the system comprising:

a display screen; and an input device, wherein the input device uses a plurality of measurement menus allowing for the selection of ultrasound measurements off of the display screen, some of the measurement menus being associated with potential conditions, at least one of the measurement menus associated with a potential condition enabling the selection of at least some of a set of suggested ultrasound measurements of the plurality of ultrasound measurements, the set of suggested measurements being appropriate for the potential condition associated with that measurement menu.

2. The system of claim 1, wherein the input device is such that all of the measurement menus associated with a potential condition do not enable the selection of other ultrasound measurements of the plurality of ultrasound measurements.

3. The system of claim 1, wherein the plurality of ultrasound measurements are ultrasound cardiac measurements.

4. The system of claim 1, wherein each measurement menu associated with any potential condition enables the selection of ultrasound measurements appropriate for the potential condition associated with that measurement menu.

5. The system of claim 4, further comprising output display screen formats for displaying results of ultrasound measurements on the display screen, the display screen formats being presented differently for different potential conditions.

6. The system of claim 1, wherein the measurements enabled by the at least one of the measurement menus use more than one ultrasound system operation mode.

7. The system of claim 1, wherein all of the measurement menus associated with a potential condition are part of a menu branch.

8. The system of claim 7, wherein each measurement in the set of suggested ultrasound measurements is selectable from menus in the menu branch.

9. The system of claim 7, wherein the menu branch comprises a group of menus including a submenu from which a measurement menu is selectable.

10. The system of claim 1, wherein the potential condition is selectable from a main menu.

11. The system of claim 1, wherein the potential condition is selectable from a sub-menu.

12. A method for providing an interactive ultrasound measurement system in which one of a plurality of ultrasound measurements can be selected, the method comprising the steps of:

providing a plurality of menu headings, at least some of the menu headings describing potential conditions; and providing a plurality of measurement menus associated with the menu headings such that some of the plurality of measurement menus are associated with potential conditions, wherein at least one of the measurement menus associated with a potential condition enables the selection of at least some of a set of suggested ultrasound measurements of the plurality of ultrasound measurements, the set of suggested ultrasound measurements being appropriate for the potential condition associated with that measurement menu.

13. The method of claim 12, wherein the menu providing step is such that all of the measurement menus associated with a potential condition do not enable the selection of other ultrasound measurements of the plurality of ultrasound measurements.

14. The method of claim 12, wherein the plurality of ultrasound measurements are ultrasound cardiac measurements.

15. The method of claim 12, wherein the menu providing step is such that each measurement menu associated with any potential condition enables the selection of ultrasound measurements appropriate for the potential condition associated with that measurement menu.

16. The method of claim 12, wherein the menu providing step is such that the measurements enabled by the at least one of the measurement menus uses more than one ultrasound system operation mode.

17. The method of claim 12, wherein the menu providing step is such that all of the measurement menus associated with a potential condition are part of a menu branch.

18. The method of claim 17, wherein the menu providing step is such that each measurement in the set of suggested ultrasound measurements is selectable from menus in the menu branch.

19. The method of claim 17, wherein the menu providing step is such that the menu branch comprises a group of menus including a submenu from which a measurement menu is selectable.

20. The method of claim 12, wherein the menu heading and menu providing steps are such that the potential condition is selectable from a main menu.

21. The method of claim 12, wherein the menu heading and menu providing steps are such that the potential condition is selectable from a sub-menu.

22. The method of claim 12, further comprising the step of providing output display screen formats for displaying results of ultrasound measurements on the display screen, the display screen formats being presented differently for different potential conditions.

23. A method for selecting ultrasound measurements using a system in which a plurality of ultrasound measurements can be selected off of a display screen, the method comprising the steps of:

selecting a measurement menu to display on the display screen, the measurement menu being associated with a potential condition and enabling the selection of suggested ultrasound measurements from the plurality of ultrasound measurements, the suggested ultrasound measurements being appropriate for the potential condition; and selecting at least one of the suggested ultrasound measurements appropriate for the potential condition.

24. The method of claim 23, further comprising making the at least one of the suggested ultrasound measurements appropriate for the potential condition.

25. The method of claim 23, wherein the measurement menu selecting step comprises selecting a sub-menu off of a main menu.

26. The method of claim 25, wherein the measurement menu selecting step comprises selecting the measurement menu off of the sub-menu.

27. The method of claim 23, wherein the measurement menu selecting step comprises selecting the measurement menu off of a main menu.

28. The method of claim 23, wherein the measurement menu selecting step is such that the measurement menu allows for the selection of less than all of the measurements appropriate for the potential condition.

* * * * *

UNITED STATES PATENT AND TRADEMARK OFFICE
CERTIFICATE OF CORRECTION

PATENT NO. : 5,553,620
DATED : September 10, 1996
INVENTOR(S) : Snider et al.

It is certified that error appears in the above-indentified patent and that said Letters Patent is hereby corrected as shown below:

In Column 4, line 44 replace:
"IVS in diasrole and systole" with

--IVS in diastole and systole--

In Column 6, line 1 replace:
"FIGS 7A-D are diagrams showing the measurements" with --FIGS 7A-B are diagrams showing the measurements--

Signed and Sealed this

First Day of April, 1997

Attest:

BRUCE LEHMAN

Attesting Officer

Commissioner of Patents and Trademarks